US006348583B1

(12) United States Patent
Segev

(10) Patent No.: US 6,348,583 B1
(45) Date of Patent: Feb. 19, 2002

(54) POLY(ETHER-THIOETHER), POLY(ETHER-SULFOXIDE) AND POLY(ETHER-SULFONE) NUCLEIC ACIDS

(75) Inventor: David Segev, Mazkeret Batya (IL)

(73) Assignee: Bio-Rad Laboratories, Inc., Hercules, CA (US)

(*) Notice: Subject to any disclaimer, the term of this patent is extended or adjusted under 35 U.S.C. 154(b) by 0 days.

(21) Appl. No.: 09/411,862

(22) Filed: Oct. 4, 1999

Related U.S. Application Data

(63) Continuation-in-part of application No. 09/384,995, filed on Aug. 20, 1999, now abandoned.

(51) Int. Cl.[7] .................... C07H 19/00; C07H 21/00; C07H 21/02; C07H 21/04; A01N 61/00
(52) U.S. Cl. ............ 536/23.1; 536/22.1; 536/24.3; 536/25.3; 536/25.32; 514/1; 514/44
(58) Field of Search ................. 536/22.1, 23.1, 536/24.3, 25.3, 25.32; 514/1, 44

(56) References Cited

FOREIGN PATENT DOCUMENTS

WO    WO 86/05518    * 9/1986

* cited by examiner

*Primary Examiner*—Jezia Riley

(57) ABSTRACT

A compound comprising a poly(ether-thioether), poly(ether-sulfoxide) or poly(ether-sulfone) backbone bearing a plurality of ligands that are individually bound to chiral carbon atoms located within the backbone, at least one of the ligands including a moiety such as a naturally occurring nucleobase, a nucleobase binding group or a DNA interchelator; a process of synthesizing the compound, monomers to be used in this process and their synthesis process and processes for using the compound in biochemistry and medicine.

11 Claims, 10 Drawing Sheets

(9 of 10 Drawing Sheet(s) Filed in Color)

ered sequences, also referred to as acyclic polynucleotide sequences; (iv) a method for synthesizing the acyclic nucleotide mimetic sequences; and (v) use of the acyclic nucleotide mimetic sequences as oligonucleotides in, for example, antisense applications and procedures.

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 4
      (B) TYPE: nucleic acid
      (C) STRANDEDNESS: single
      (D) TOPOLOGY: linear (xi) SEQUENCE DESCRIPTION: SEQ ID NO: 1:

NNNN                                                              4

(2) INFORMATION FOR SEQ ID NO: 2:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 2:

NNNN                                                                            4

(2) INFORMATION FOR SEQ ID NO: 3:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 3:

NNNN                                                                            4

(2) INFORMATION FOR SEQ ID NO: 4:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 4:

NNNN                                                                            4

(2) INFORMATION FOR SEQ ID NO: 5:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 5:

NNNN                                                                            4

(2) INFORMATION FOR SEQ ID NO: 6:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 6:

NNNN                                                                            4

(2) INFORMATION FOR SEQ ID NO: 7:

(i) SEQUENCE CHARACTERISTICS:
            (A) LENGTH: 4
            (B) TYPE: nucleic acid
            (C) STRANDEDNESS: single
            (D) TOPOLOGY: linear (xi) SEQUENCE DESCRIPTION: SEQ ID NO: 7:

NNNN                                                                            4

(2) INFORMATION FOR SEQ ID NO: 8:

```
    (i) SEQUENCE CHARACTERISTICS:
        (A) LENGTH: 4
        (B) TYPE: nucleic acid
        (C) STRANDEDNESS: single
        (D) TOPOLOGY: linear (xi) SEQUENCE DESCRIPTION: SEQ ID NO: 8:

NNNN                                                                        4

(2) INFORMATION FOR SEQ ID NO: 9:

(i) SEQUENCE CHARACTERISTICS:
        (A) LENGTH: 4
        (B) TYPE: nucleic acid
        (C) STRANDEDNESS: single
        (D) TOPOLOGY: linear (xi) SEQUENCE DESCRIPTION: SEQ ID NO: 9:

NNNN                                                                        4

(2) INFORMATION FOR SEQ ID NO: 10:

(i) SEQUENCE CHARACTERISTICS:
        (A) LENGTH: 3
        (B) TYPE: nucleic acid
        (C) STRANDEDNESS: single
        (D) TOPOLOGY: linear (xi) SEQUENCE DESCRIPTION: SEQ ID NO: 10:

WSW                                                                         3

(2) INFORMATION FOR SEQ ID NO: 11:

(i) SEQUENCE CHARACTERISTICS:
        (A) LENGTH: 3
        (B) TYPE: nucleic acid
        (C) STRANDEDNESS: single
        (D) TOPOLOGY: linear (xi) SEQUENCE DESCRIPTION: SEQ ID NO: 11:

WSW                                                                         3

(2) INFORMATION FOR SEQ ID NO: 12:

(i) SEQUENCE CHARACTERISTICS:
        (A) LENGTH: 3
        (B) TYPE: nucleic acid
        (C) STRANDEDNESS: single
        (D) TOPOLOGY: linear (xi) SEQUENCE DESCRIPTION: SEQ ID NO: 12:

WSW                                                                         3

(2) INFORMATION FOR SEQ ID NO: 13:

(i) SEQUENCE CHARACTERISTICS:
        (A) LENGTH: 3
        (B) TYPE: nucleic acid
        (C) STRANDEDNESS: single
        (D) TOPOLOGY: linear (xi) SEQUENCE DESCRIPTION: SEQ ID NO: 13:

WSW                                                                         3

(2) INFORMATION FOR SEQ ID NO: 14:

(i) SEQUENCE CHARACTERISTICS:
```

```
        (A) LENGTH: 3
        (B) TYPE: nucleic acid
        (C) STRANDEDNESS: single
        (D) TOPOLOGY: linear (xi) SEQUENCE DESCRIPTION: SEQ ID NO: 14:

WSW                                                                         3

(2) INFORMATION FOR SEQ ID NO: 15:

(i) SEQUENCE CHARACTERISTICS:
        (A) LENGTH: 2
        (B) TYPE: nucleic acid
        (C) STRANDEDNESS: single
        (D) TOPOLOGY: linear (xi) SEQUENCE DESCRIPTION: SEQ ID NO: 15:

NN                                                                          2

(2) INFORMATION FOR SEQ ID NO: 16:

(i) SEQUENCE CHARACTERISTICS:
        (A) LENGTH: 2
        (B) TYPE: nucleic acid
        (C) STRANDEDNESS: single
        (D) TOPOLOGY: linear (xi) SEQUENCE DESCRIPTION: SEQ ID NO: 16:

NN                                                                          2

(2) INFORMATION FOR SEQ ID NO: 17:

(i) SEQUENCE CHARACTERISTICS:
        (A) LENGTH: 4
        (B) TYPE: nucleic acid
        (C) STRANDEDNESS: double
        (D) TOPOLOGY: linear (xi) SEQUENCE DESCRIPTION: SEQ ID NO: 17:

TTTT                                                                        4

(2) INFORMATION FOR SEQ ID NO: 18:

(i) SEQUENCE CHARACTERISTICS:
        (A) LENGTH: 10
        (B) TYPE: nucleic acid
        (C) STRANDEDNESS: double
        (D) TOPOLOGY: linear (xi) SEQUENCE DESCRIPTION: SEQ ID NO: 18:

TTTTTTTTTT                                                                 10

(2) INFORMATION FOR SEQ ID NO: 19:

(i) SEQUENCE CHARACTERISTICS:
        (A) LENGTH: 12
        (B) TYPE: nucleic acid
        (C) STRANDEDNESS: double
        (D) TOPOLOGY: linear (xi) SEQUENCE DESCRIPTION: SEQ ID NO: 19:

TTTTTTTTTT TT                                                              12

(2) INFORMATION FOR SEQ ID NO: 20:

(i) SEQUENCE CHARACTERISTICS:
        (A) LENGTH: 12
```

```
            (B) TYPE: nucleic acid
            (C) STRANDEDNESS: double
            (D) TOPOLOGY: linear (xi) SEQUENCE DESCRIPTION: SEQ ID NO: 20:

TTTTTTTTTT TT                                                              12

(2) INFORMATION FOR SEQ ID NO: 21:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 21:

CTCTCTCTCT CTCTCT                                                          16

(2) INFORMATION FOR SEQ ID NO: 22:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 22:

GAGAGAGAGA GAGAGA                                                          16
```

POLY(ETHER-THIOETHER), POLY(ETHER-SULFOXIDE) AND POLY(ETHER-SULFONE) NUCLEIC ACIDS This is a continuation-in-part of U.S. patent application Ser. No. 09/384,995, filed Aug. 20, 1999, now abandoned.

FIELD AND BACKGROUND OF THE INVENTION

The present invention relates, in general, to nucleotide mimetics and their derived nucleic acid mimetics, methods for the construction of both and the use of the nucleic acid mimetics in biochemistry and medicine. More particularly, the present invention relates to (i) acyclic nucleotide mimetics, also referred to as acyclic nucleotides, based upon a poly(ether-thioether), poly(ether-sulfoxide) or poly(ether-sulfone) backbone; (ii) a method for synthesizing the acyclic nucleotide mimetics; (iii) acyclic nucleotide mimetic sequences, also referred to as acyclic polynucleotide sequences; (iv) a method for synthesizing the acyclic nucleotide mimetic sequences; and (v) use of the acyclic nucleotide mimetic sequences as oligonucleotides in, for example, antisense applications and procedures.

An antisense oligonucleotide (e.g., antisense oligodeoxyribonucleotide) may bind its target nucleic acid either by Watson-Crick base pairing or Hoogsteen and anti-Hoogsteen base pairing. To this effect see, Thuong and Helene (1993) Sequence specific recognition and modification of double helical DNA by oligonucleotides Angev. Chem. Int. Ed. Engl. 32:666. According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triplex structure.

According to both the Watson-Crick and the Hoogsteen base pairing models, antisense oligonucleotides have the potential to regulate gene expression and to disrupt the essential functions of the nucleic acids. Therefore, antisense oligonucleotides have possible uses in modulating a wide range of diseases.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, gene therapy or the regulation of transcription or translation levels.

Gene expression involves few distinct and well-regulated steps. The first major step of gene expression involves transcription of a messenger RNA (mRNA) which is an RNA sequence complementary to the antisense (i.e., −) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more protein transcription factors to the promoter sequence. Additional proteins, which bind at or close to the promoter sequence, may upregulate transcription and are known as enhancers. Other proteins, which bind to or close to the promoter, but whose binding prohibits action of RNA polymerase, are known as repressors.

There is also evidence that in some cases gene expression is downregulated by endogenous antisense RNA repressors that bind a complementary mRNA transcript and thereby prevent its translation into a functional protein. To this effect see Green et al. (1986) The role of antisense RNA in gene regulation. Ann. Rev. Biochem. 55:569.

Thus, gene expression is typically upregulated by transcription factors and enhancers and downregulated by repressors.

However, in many disease situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites., bacteria or viruses, the disease progression depends on expression of the pathogen genes, this phenomenon may also be considered as far as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription. To this effect see, Thuong and Helene (1993) Sequence specific recognition and modification of double helical DNA by oligonucleotides Angev. Chem. Int. Ed. Engl. 32:666.

At the transcript level, antisense oligonucleotides or analogs that bind target mRNA molecules lead to the enzymatic cleavage of the hybrid by intracellular RNase H. To this effect see Dash et al. (1987) Proc. Natl. Acad. Sci. USA, 84:7896. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. To this effect see Chiang et al. (1991) Antisense oligonucleotides inhibit intercellular adhesion molecule 1 expression by two distinct mechanisms. J. Biol. Chem. 266:18162. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, as described by Paterson et al. (1977) Proc. Natl. Acad. Sci. USA, 74:4370, a phenomenon known in the art as hybridization arrest, disabling the translation of such mRNAs.

Thus, antisense sequences, which as described hereinabove, may arrest the expression of any endogenous and/or exogenous gene depending on their specific sequence, attracted much attention by scientists and pharmacologists who were devoted at developing the antisense approach into a new pharmacological tool. To this effect see Cohen (1992) Oligonucleotide therapeutics. Trends in Biotechnology, 10:87.

For example, several antisense oligonucleotides have been shown to arrest hematopoietic cell proliferation (Szczylik et al (1991) Selective inhibition of leukemia cell proliferation by BCR-ABL antisense oligodeoxynucleotides. Science 253:562), growth (Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351), entry into the S phase of the cell cycle (Heikhila et al. (1987) A c-myc antisense oligodeoxynucleotide inhibits entry into S phase but not progress from G(0) to G(1). Nature, 328:445), reduced survival (Reed et al. (1990) Antisense mediated inhibition of BCL2 prooncogene expression and leukemic cell growth and survival: comparison of phosphodiester and phosphorothioate oligodeoxynucleotides. Cancer Res. 50:6565) and prevent receptor mediated responses (Burch and Mahan (1991) Oligodeoxynucleotides antisense to the interleukin I receptor m RNA block the effects of interleukin I in cultured murine and human fibroblasts and in mice. J. Clin. Invest. 88:1190). For use of antisense oligonucleotides as antiviral agents the reader is referred to Agrawal (1992) Antisense oligonucleotides as antiviral agents. TIBTECH 10:152.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters, see, Uhlmann et al. (1990) Chem. Rev. 90:544.

Thus, it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives. For further details the reader is referred to Cook (1991) Medicinal chemistry of antisense oligonucleotides—future opportunities. Anti-Cancer Drug Design 6:585.

International patent application WO 86/05518 broadly claims a polymeric composition effective to bind to a single-stranded polynucleotide containing a target sequence of bases. The composition is said to comprise non-homopolymeric, substantially stereoregular polymer molecules of the form:

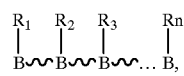

(SEQ ID NO:1) where:
(a) R1–Rn are recognition moieties selected from purine, purine-like, pyrimidine, and pyrimidine like heterocycles effective to bind by Watson/Crick pairing to corresponding, in-sequence bases in the target sequence;
(b) n is such that the total number of Watson/Crick hydrogen bonds formed between a polymer molecule and target sequence is at least about 15;
(c) B~B are backbone moieties joined predominantly by chemically stable, substantially uncharged, predominantly achiral linkages;
(d) the backbone moiety length ranges from 5 to 7 atoms if the backbone moieties have a cyclic structure, and ranges from 4 to 6 atoms if the backbone moieties have an acyclic structure; and
(e) the backbone moieties support the recognition moieties at position which allow Watson-Crick base pairing between the recognition moieties and the corresponding, in-sequence bases of the target sequence.

According to WO 86/05518, the recognition moieties are various natural nucleobases and nucleobase-analogs and the backbone moieties are either cyclic backbone moieties comprising furan or morpholine rings or acyclic backbone moieties of the following forms:

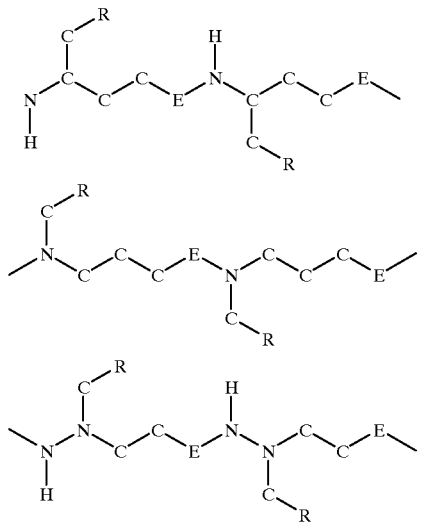

where E is —CO— or —SO$_2$—. The specification of the application provides general descriptions for the synthesis of subunits, for backbone coupling reactions, and for polymer assembly strategies. Although WO 86/05518 indicates that the claimed polymer compositions can bind target sequences and, as a result, have possible diagnostic and therapeutic applications, the application contains no data relating to the binding capabilities of a claimed polymer.

International patent application WO 86/05519 claims diagnostic reagents and systems that comprise polymers described in WO 86/05518, but attached to a solid support.

International patent application WO 89/12060 claims various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). However, the application provides no data supporting the specific binding of an oligonucleotide analog to a target oligonucleotide.

Nielsen et al. (1991) Science 254:1497, and International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. To this effect of PNA heterohybrids see Biotechnology research news (1993) Can DNA mimetics improve on the real thing? Science 262:1647.

PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal. However, there are some major drawbacks associated with the PNA approach. One drawback is that, at least in test-tube cultures, PNA molecules do not penetrate through cell membranes, not even to the limited extent natural short DNA and RNA segments do. The second drawback is side effects, which are encountered with toxicity. Because PNAs bind so strongly to target sequences, they lack the specificity of their natural counterparts and end up binding not just to target sequences but also to other strands of DNA, RNA or even proteins, incapacitating the cell in unforeseen ways.

U.S. Pat. No. 5,908,845 to Segev describes nucleic acid mimetics consisting of a polyether backbone, bearing a plurality of ligands, such as nucleobases or analogs thereof, which are able to hybridize to complementary DNA or RNA sequences. More specifically, various building blocks based upon polyether backbone, such as polyethylene glycol (PEG), for synthesizing nucleotide mimetics, as well as oligonucleotide mimetics formed by joining such building blocks in a defined manner, methods for synthesizing both and the use of both in biochemistry and medicine are described. According to U.S. Pat. No. 5,908,845, the oligonucleotide mimetics are of the following optional forms:

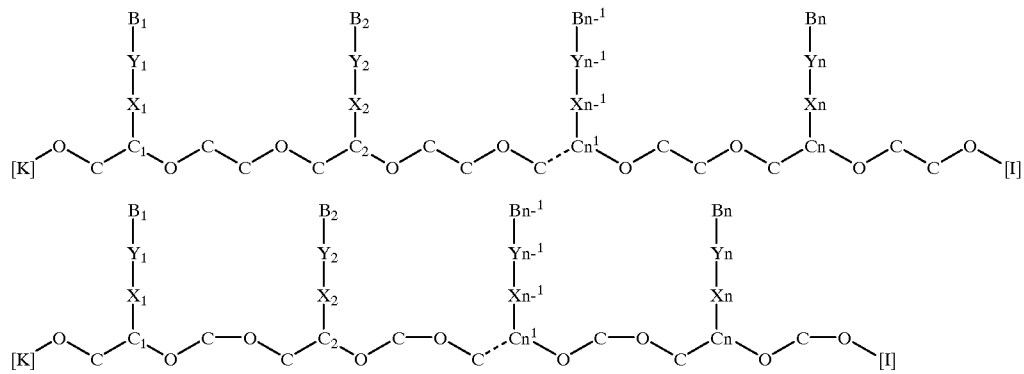

(SEQ ID NOs:2 and 3) where n is an integer greater than one, each of B1–Bn is independently a chemical functionality group, such as, but not limited to, a naturally occurring nucleobase, a nucleobase binding group or a DNA intercelator, each of Y1–Yn is a first linker group, each of X1–Xn is a second linker group, C1–Cn are chiral carbon atoms and [K] and [I] are a first and second exoconjugates.

Although the specification of U.S. Pat. No. 5,908,845 provides general description for the synthesis of the subunits for backbone coupling reactions and for polymer assembly and modifications strategies thereof, U.S. Pat. No. 5,908,845 includes no experimental data as to the feasibility of the synthetic procedure itself. While attempting to synthesize the above polyether nucleic acids, it was realized that synthesis yields are less than sufficient for efficient mass production.

There is thus a widely recognized need for, and it would be highly advantageous to have, oligonucleotide analogs devoid of these drawbacks, and which are characterized by (i) ease of synthetic procedure and proven synthetic efficiency; and which are further characterized by properties common to the above described polyether nucleic acids, such as (ii) sufficient specificity in binding to target sequences; (iii) solubility in water; (iv) stability against intra- and extracellular nucleases; (v) capability of penetrating through cell membranes; and (vi) when used to treat an organism, low toxicity, properties that collectively render an oligonucleotide analog highly suitable as an antisense therapeutic drug.

SUMMARY OF THE INVENTION

It is one object of the present invention to provide compounds that bind dsDNA, ssDNA and/or RNA strands to form stable hybrids therewith.

It is a further object of the invention to provide compounds that bind dsDNA, ssDNA and/or RNA strands more strongly then the corresponding DNA, yet less strongly then PNA.

It is another object to provide compounds wherein naturally-occurring nucleobases or other nucleobase-binding moieties or instead of some or all the base(s), a linker arm which terminates with a chemical functionality groups, are covalently bound to a poly(ether-thioether), poly(ether-sulfoxide) or poly(ether-sulfone) backbone.

It is yet another object to provide compounds other than RNA or PNA that can bind under in vivo conditions one strand of a double-stranded polynucleotide, thereby displacing the other strand.

It is yet a further object of the invention to provide a method for fabricating building blocks suitable for the fabrication of such compounds.

It is still a further object of the invention to provide a method for fabricating such compounds from their building blocks.

It is still another object to provide therapeutic and prophylactic methods that employ such compounds.

Additional objectives of the inventions are further described hereinbelow.

According to one aspect of the present invention there is provided a compound comprising a poly(ether-thioether) backbone having a plurality of chiral carbon atoms, the poly(ether-thioether) backbone bearing a plurality of ligands being individually bound to the chiral carbon atoms, the ligands including a moiety selected from the group consisting of a naturally occurring nucleobase and a nucleobase binding group.

According to another aspect of the present invention there is provided a compound comprising a poly(ether-sulfoxide) or a poly(ether-sulfone) backbone having a plurality of chiral carbon atoms, the poly(ether-sulfoxide) or poly(ether-sulfone) backbone bearing a plurality of ligands being individually bound to said chiral carbon atoms, said ligands including a moiety selected from the group consisting of a naturally occurring nucleobase and a nucleobase binding group.

According to further features in preferred embodiments of the invention described below one or more linker arms which terminate with chemical functionality group(s) replace one or more of the naturally occurring nucleobase(s) and/or nucleobase binding group(s).

According to further features in preferred embodiments of the invention described below, the chiral carbon atoms are separated from one another in the backbone by from four to six intervening atoms.

According to another aspect of the present invention there is provided a compound having the formula:

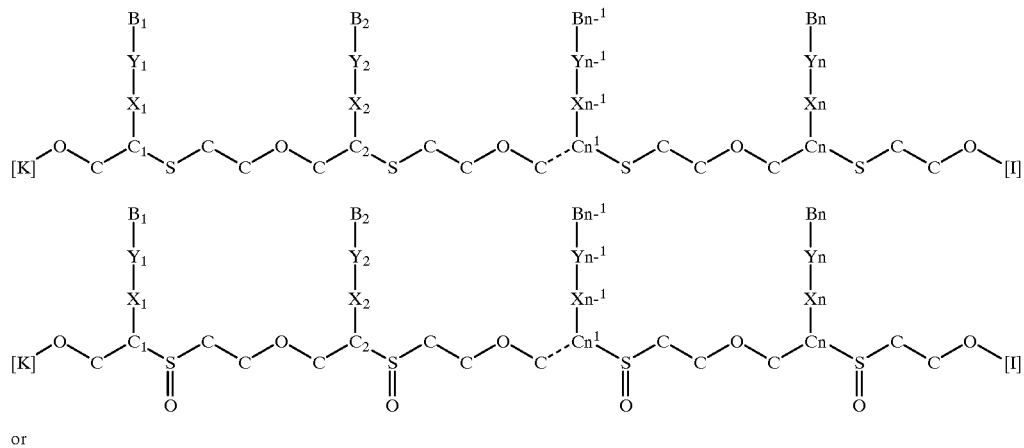

or

-continued

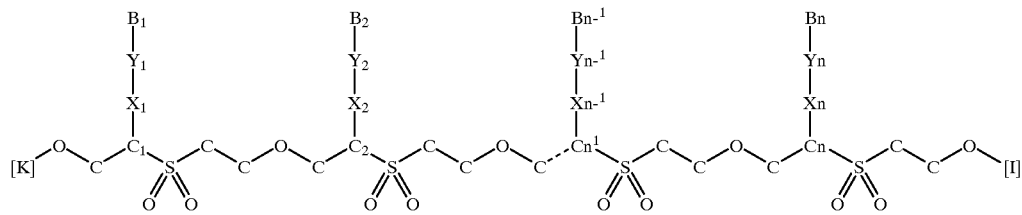

(SEQ ID NOs:4–6) wherein:
  n is an integer greater than one;
  each of B1, B2, Bn–1 and Bn is a chemical functionality group independently selected from the group consisting of a naturally occurring nucleobase and a nucleobase binding group.
  each of Y1, Y2, Yn–1 and Yn is a first linker group;
  each of X1, X2, Xn–1 and Xn is a second linker group;
  C1, C2, Cn–1 and Cn are chiral carbon atoms; and
  [K] and [I] are a first and a second exoconjugates.

According to further features in preferred embodiments of the invention described below, one or more linker arms which terminate with chemical functionality group(s) replace one or more of the naturally occurring nucleobase(s) and/or nucleobase binding group(s).

According to further features in preferred embodiments of the invention described below, each of the Y1-X1, Y2-X2, Yn–1-Xn–1 and Yn-Xn first-second linker groups is a single bond.

According to still further features in the described preferred embodiments each of the Y1, Y2, Yn–1 and Yn first linker groups is independently selected from the group consisting of an alkyl group, a phosphate group, a (C2–C4) alkylene chain, a (C2–C4) substituted alkylene chain and a single bond.

According to still further features in the described preferred embodiments each of the Y1, Y2, Yn–1 and Yn first linker groups is independently selected from the group consisting of a methylene group and a C-alkanoyl group which includes an alkyl of k carbons and a carbonyl moiety, whereas k is an integer between 2 and 20.

According to still further features in the described preferred embodiments each of the X1, X2, Xn–1 and Xn second linker groups is independently selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

According to still further features in the described preferred embodiments m percents of the chiral carbons are in an S configuration or alternatively an R configuration, wherein m is selected from the group consisting of 90–95%, 96–98%, 99% and greater than 99%.

According to still further features in the described preferred embodiments [K] and [I] are each a polyethylene glycol moiety.

According to still further features in the described preferred embodiments the compound has the formula:

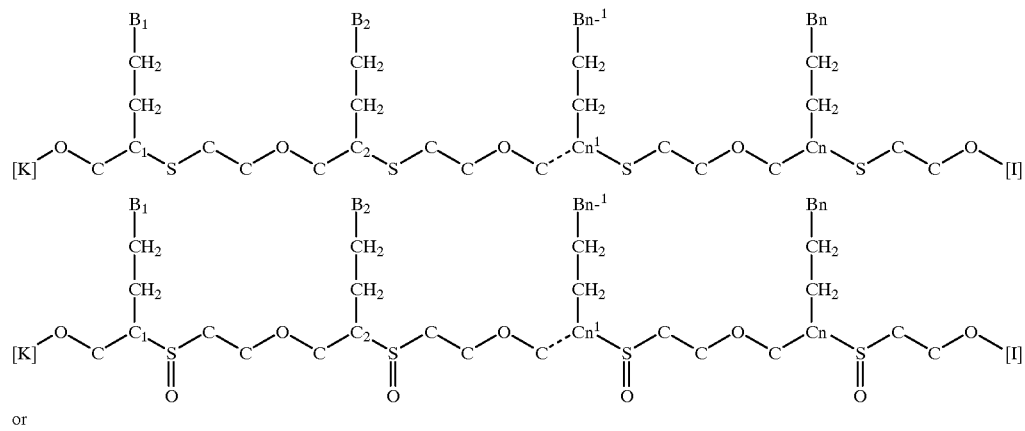

or

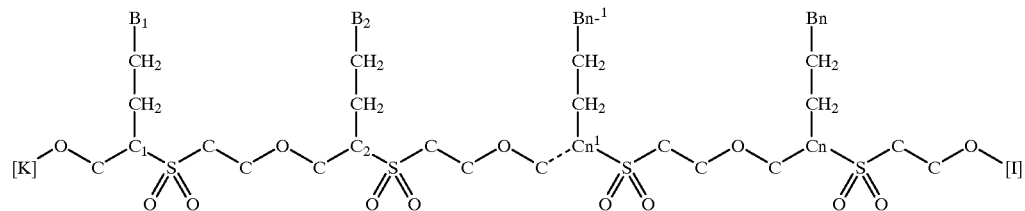

(SEQ ID NOs:7–9)

According to yet another aspect of the present invention there is provided a compound having a formula:

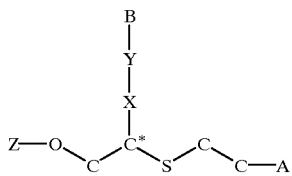

wherein:

B is a chemical functionality group, selected from the group consisting of a naturally occurring nucleobase, a nucleobase binding group and a chemical functionality group attached via a linker arm;

Y is a first linker group;

X is a second linker group;

C* is a chiral carbon atom;

Z is a first protecting group; and

A is a leaving group;

According to further features in preferred embodiments of the invention described below, the Y-X first-second linker group is a single bond.

According to still further features in the described preferred embodiments the Y first linker group is selected from the group consisting of an alkyl group, a phosphate group, a (C2–C4) alkylene chain, a (C2–C4) substituted alkylene chain and a single bond.

According to still further features in the described preferred embodiments the Y first linker group is selected from the group consisting of a methylene group and a C-alkanoyl group.

According to still further features in the described preferred embodiments the X second linker group is selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

According to still further features in the described preferred embodiments should the nucleobase include an amino group, the amino group is protected by a second protecting group.

According to still further features in the described preferred embodiments the Z protecting group is selected from the group consisting of a dimethoxytrityl group, a trityl group, a monomethoxytrityl group and a silyl group.

According to still further features in the described preferred embodiments the A leaving group is selected from the group consisting of a halide group, a sulfonate group, an ammonium derivative, a radical moiety that could be replaced by SN1 or SN2 mechanisms.

According to still further features in the described preferred embodiments the second protecting group is selected from the group consisting of a methylbenzylether group, a benzamido group, an isobutyramido group, a t-butoxycarbonyl group, a fluorenylmethyloxycarbonyl group and an acid labile group which is not cleaved by reagents that cleave the Z protecting group.

According to still further features in the described preferred embodiments the compound of has the formula:

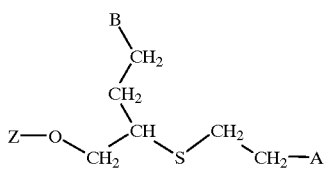

According to still another aspect of the present invention there is provided a process of preparing the above described polymeric compound, the process comprising the steps of (a) obtaining monomers each of the monomers having an ether moiety and a thioether moiety, the ether moiety including at least one etheric bond, the thioether moiety including at least one thioetherie bond, each of the monomers further including at least one chiral carbon atom to which a functionality group being linked, the functionality group being selected from the group consisting of a naturally occurring nucleobase and a nucleobase binding group; (b) attaching a first monomer of the monomers to a solid support; and (c) sequentially condensing monomers in a predetermined sequence to the first monomer for obtaining a polymer of condensed monomers and optionally (d) oxidizing sulfide moieties to sulfoxide and/or to sulfone. Alternatively, monomers may be attached through K and/or I moieties to a polymeric chain, such as a polyethylene glycol unit of varying lengths, itself being attached to a solid support. It will be appreciated that steps (b) and (c) above can alternatively be performed in solution rather than on a solid polymeric support. The resulting polymeric product can thereafter be purified by chromatographic methods well known in the art, such as high performance liquid chromatography (HPLC), TLC and the like.

According to an additional aspect of the present invention there is provided a process of sequence specific hybridization comprising the step of contacting a double stranded polynucleotide with the above described polymeric compound, so that the compound binds in a sequence specific manner to one strand of the polynucleotide, thereby displacing the other strand.

According to yet an additional aspect of the present invention there is provided a process of sequence specific hybridization comprising the step of contacting a single-stranded polynucleotide with the above described polymeric compound, so that the compound binds in a sequence specific manner to the polynucleotide.

According to still an additional aspect of the present invention there is provided a process of modulating the expression of a gene in an organism comprising the step of administering to the organism the above described polymeric compound, such that the compound binds in a sequence specific manner DNA or RNA deriving from the gene.

According to further features in preferred embodiments of the invention described below the modulation includes inhibiting transcription of the gene.

According to still further features in the described preferred embodiments the modulation includes inhibiting replication of the gene.

According to still further features in the described preferred embodiments the modulation includes inhibiting translation of the RNA of the gene.

According to a further aspect of the present invention there is provided a process of treating a condition associated with undesired protein production in an organism, the process comprising the step of contacting the organism with an effective amount of the above described polymeric compound, the compound specifically binds with DNA or RNA deriving from a gene controlling the protein production.

According to yet a further aspect of the present invention there is provided a process of inducing degradation of DNA or RNA in cells of an organism, comprising the steps of administering to the organism the above described polymeric compound, the compound specifically binds to the DNA or RNA.

According to still a further aspect of the present invention there is provided a process of killing cells or viruses comprising the step of contacting the cells or viruses with the above described polymeric compound, the compound specifically binds to a portion of the genome or to RNA derived therefrom of the cells or viruses.

According to another aspect of the present invention there is provided a pharmaceutical composition comprising, as an active ingredient, the above described polymeric compound, and at least one pharmaceutically effective carrier, binder, thickener, diluent, buffer, preservative or surface active agent.

The present invention successfully addresses the shortcomings of the presently known configurations by providing an oligonucleotide analog characterized by (i) sufficient specificity in binding its target sequence; (ii) solubility in water; (iii) stability against intra- and extracellular nucleases; (iv) capability of penetrating through the cell membrane; and (v) when used to treat an organism, low toxicity, properties collectively rendering the oligonucleotide analog of the present invention highly suitable as an antisense therapeutic is drug, and, above all being readily sythesizable.

BRIEF DESCRIPTION OF THE DRAWINGS

The file of this patent contains at least one drawing executed in color. Copies of theis patent with color drawing (s) will be provided by the Patent and Trademark Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
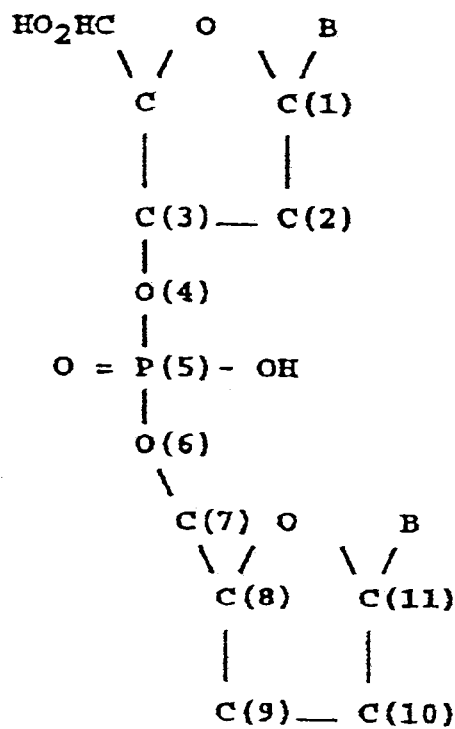
Figure 1B:
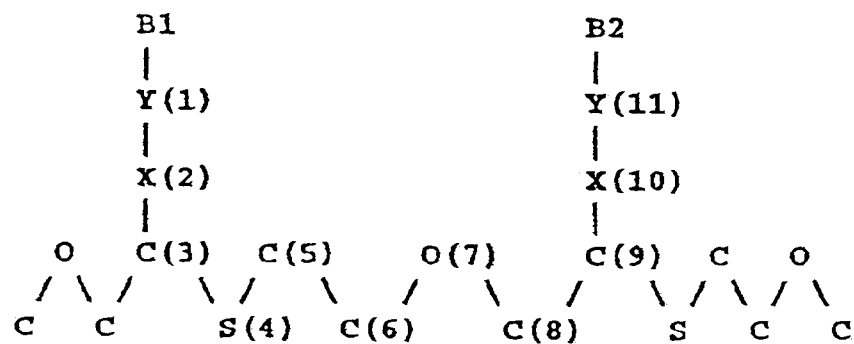
Figure 2:
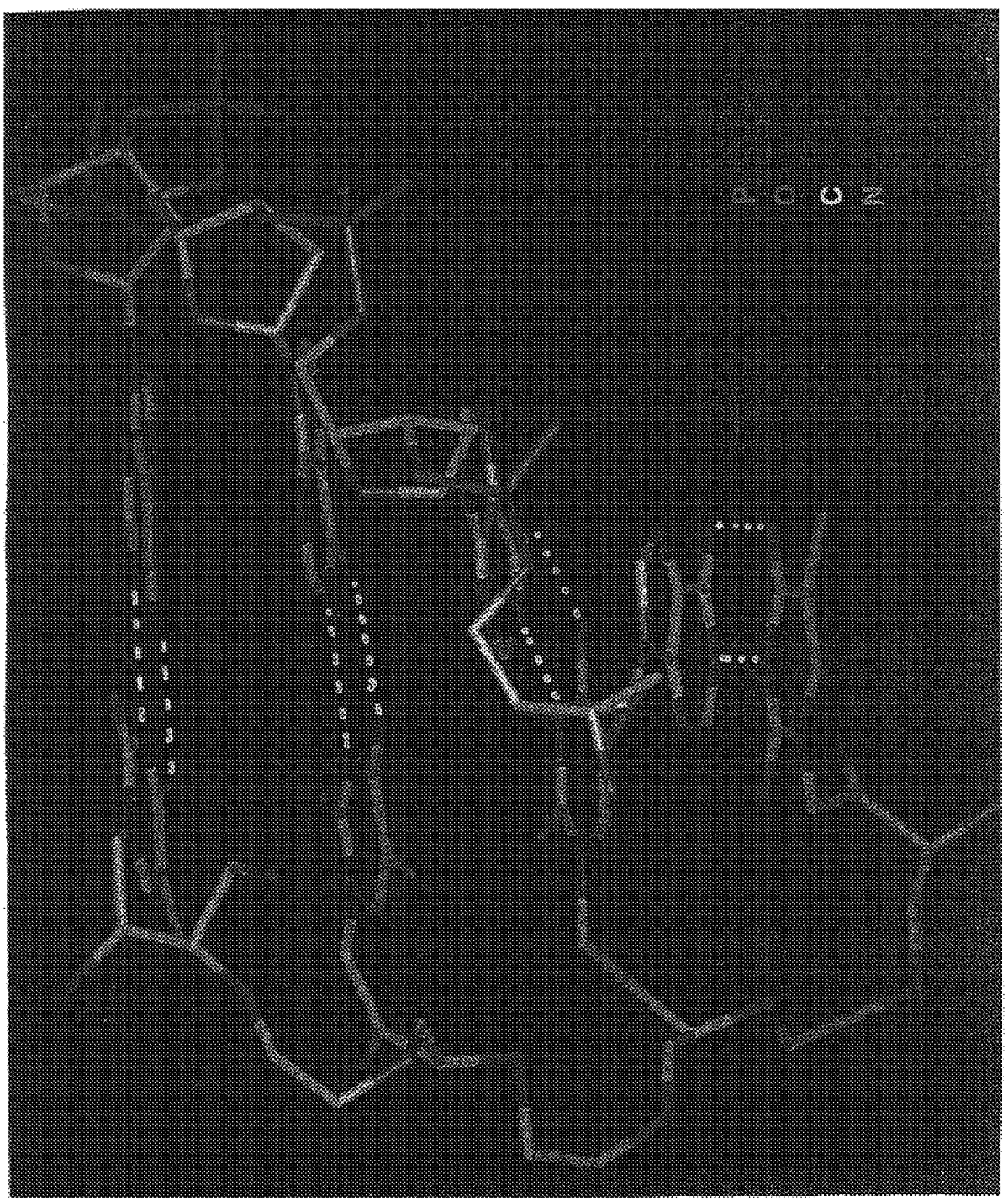
Figure 3:
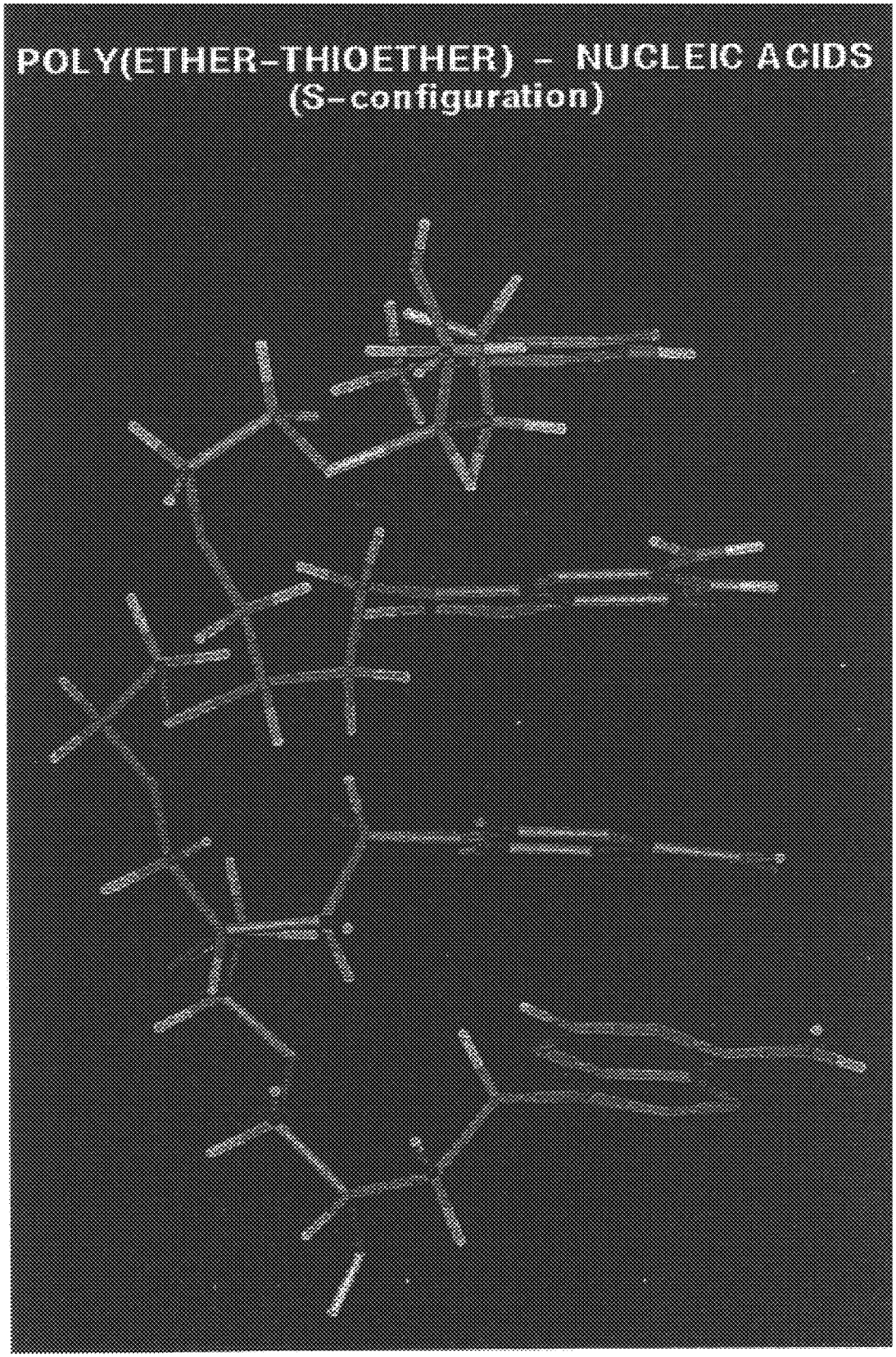
Figure 4:
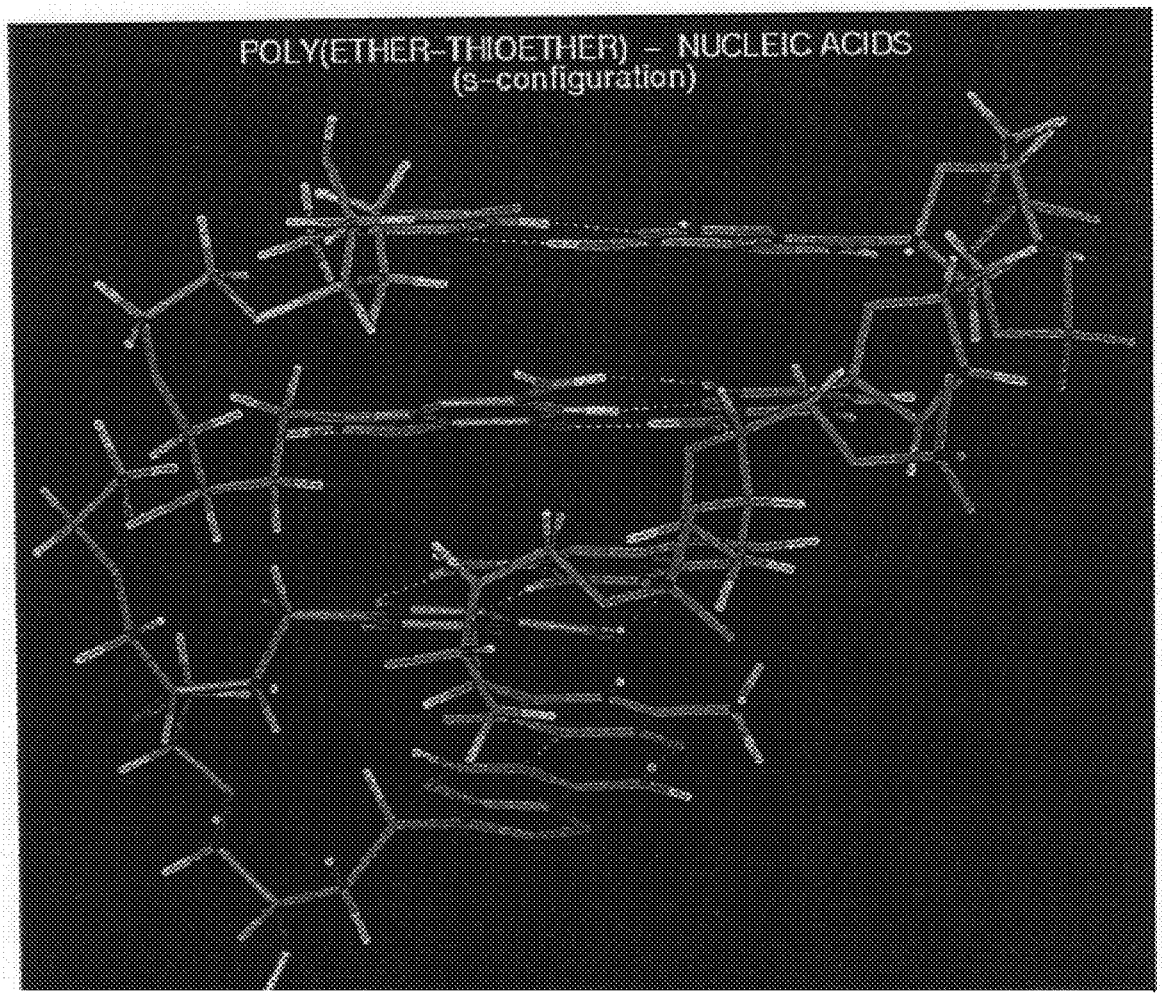
Figure 5:
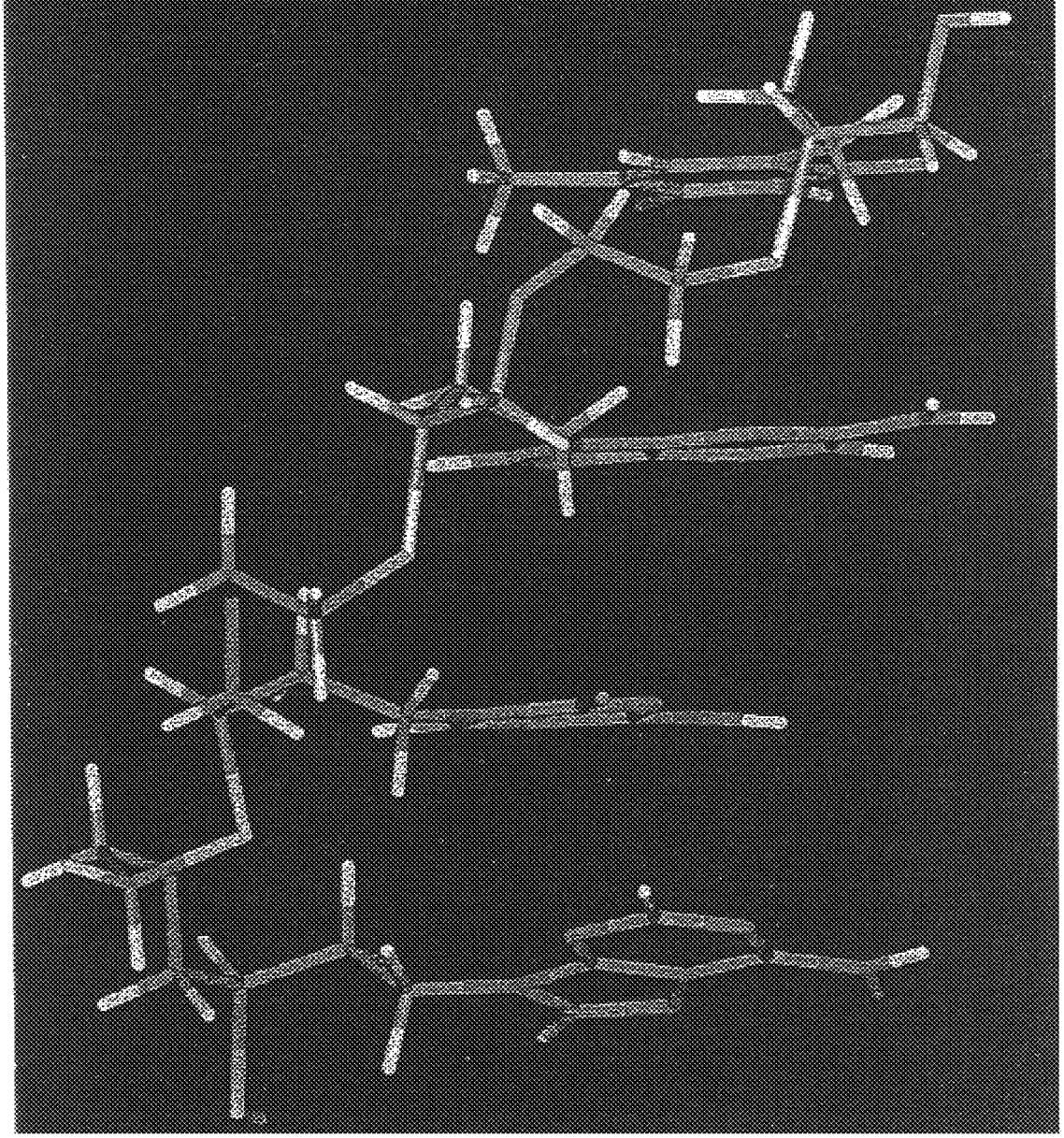
Figure 6:
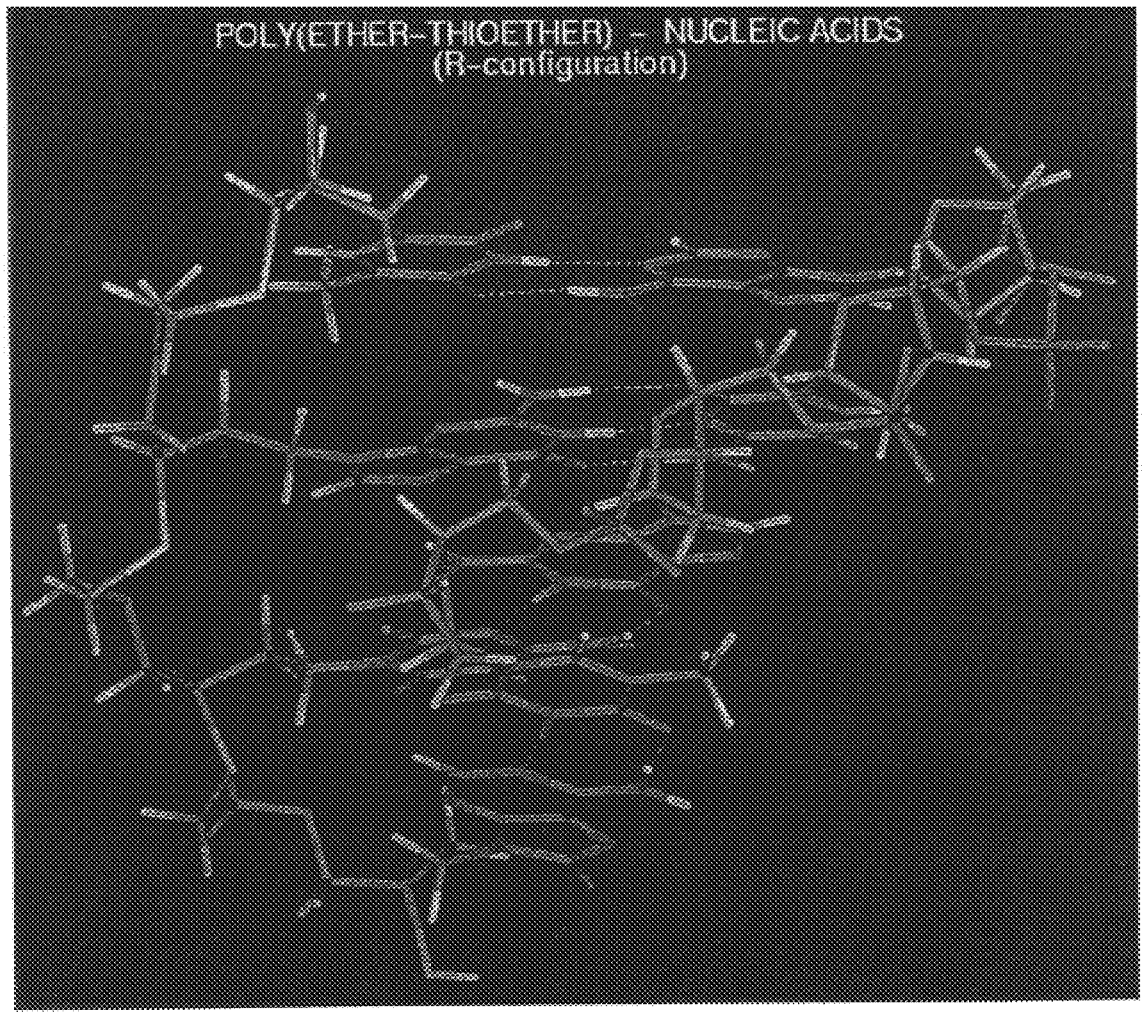
Figure 7:
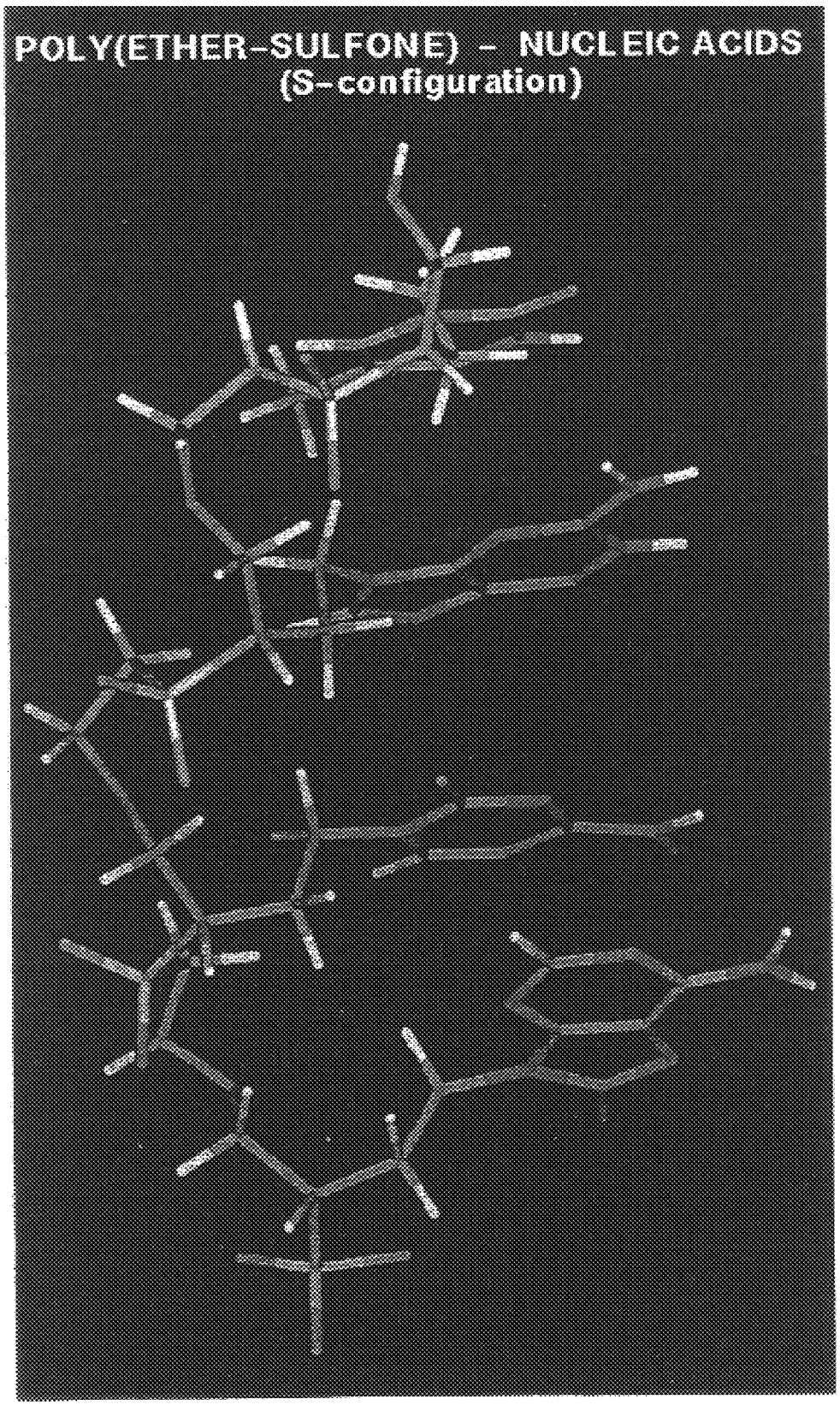
Figure 8:
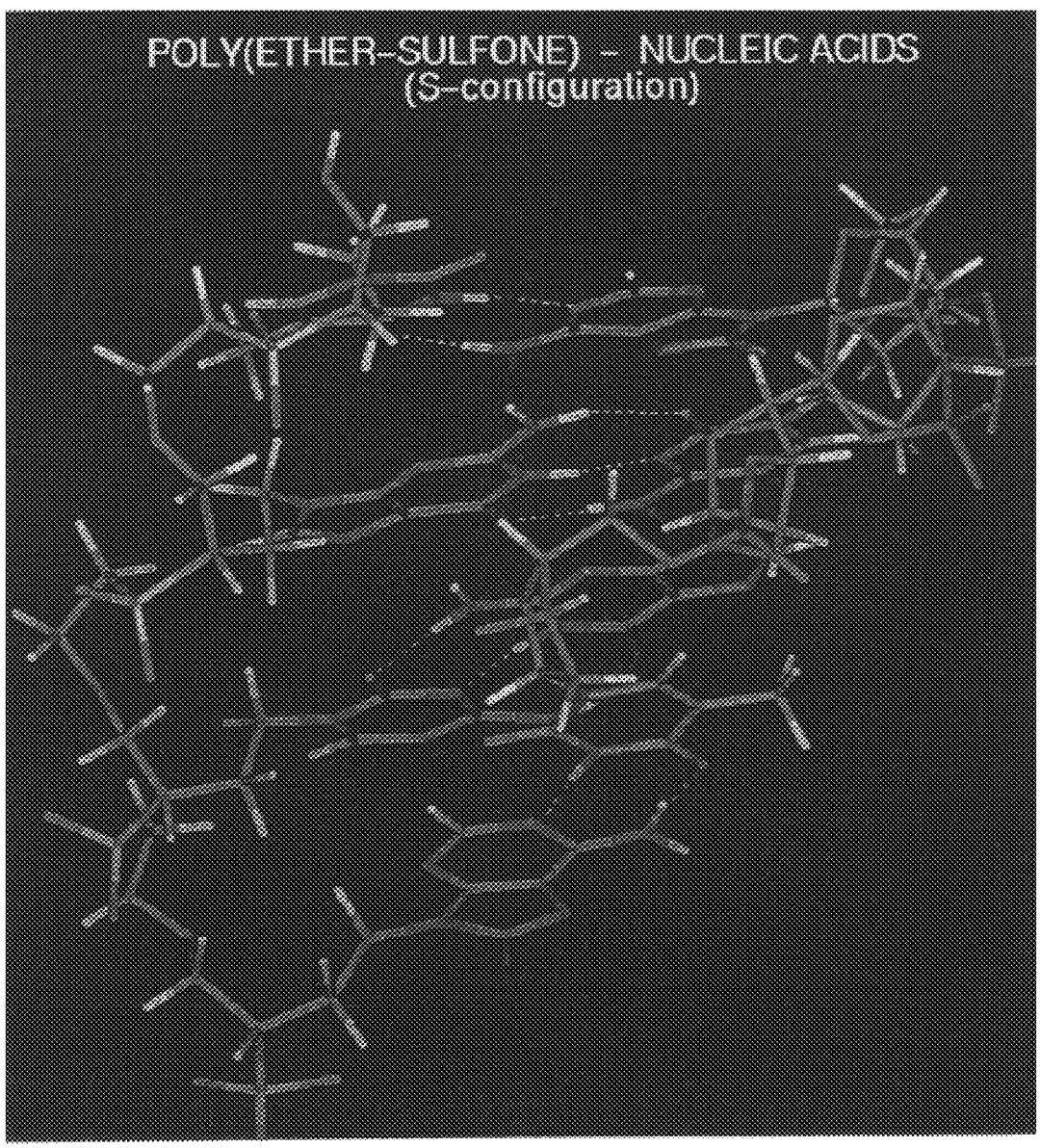
Figure 9:
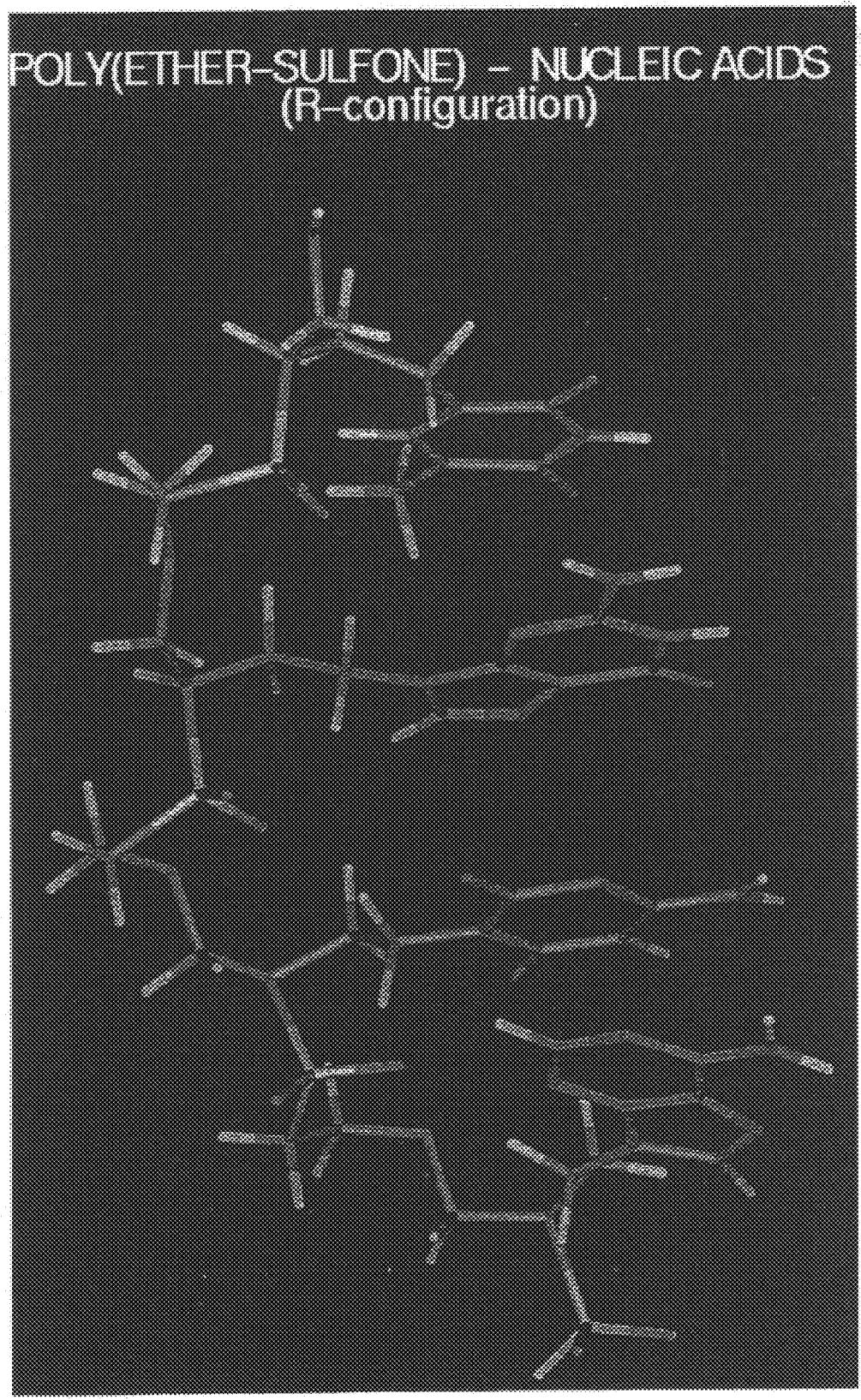
Figure 10:
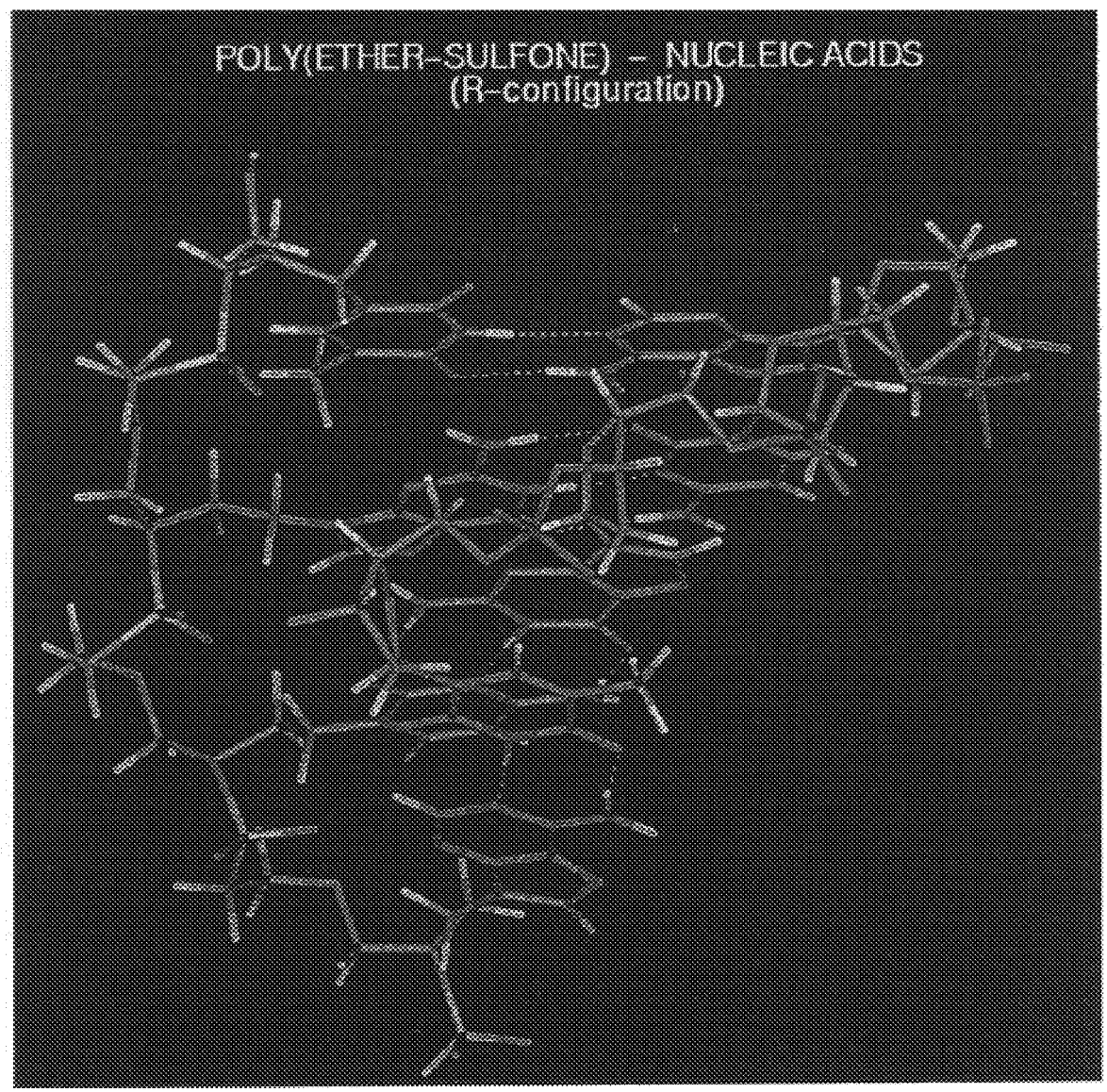

FIGS. 1a–b depicts the eleven atoms separating nucleobases on (a) prior art DNA and (b) a poly(ether-thioether) nucleic acid compound according to the present invention;

FIG. 2 is a molecular model presenting hybridization of a prior art tetra-thymine-polyether nucleic acid compound having eleven atoms between adjacent B functionality groups according to U.S. Pat. No. 5,908,845 with natural tetra-adenine-ssDNA;

FIG. 3 is a molecular model presenting a single strand molecule of poly(ether-thioether) nucleic acid having S configuration according to the present invention;

FIG. 4 is a molecular model presenting a double strand molecule of poly(ether-thioether) nucleic acid having S configuration according to the present invention, hydrogen bonds are marked by dashed lines;

FIG. 5 is a molecular model presenting a single strand molecule of poly(ether-thioether) nucleic acid having R configuration according to the present invention;

FIG. 6 is a molecular model presenting a double strand molecule of poly(ether-thioether) nucleic acid having R configuration according to the present invention, hydrogen bonds are marked by dashed lines;

FIG. 7 is a molecular model presenting a single strand molecule of poly(ether-sulfone) nucleic acid having S configuration according to the present invention;

FIG. 8 is a molecular model presenting a double strand molecule of poly(ether-sulfone) nucleic acid having S configuration according to the present invention, hydrogen bonds are marked by dashed lines;

FIG. 9 is a molecular model presenting a single strand molecule of poly(ether-sulfone) nucleic acid having R configuration according to the present invention; and FIG. 10 is a molecular model presenting a double strand molecule of poly(ether-sulfone) nucleic acid having R configuration according to the present invention, hydrogen bonds are marked by dashed lines.

DESCRIPTION OF THE PREFERRED EMBODIMENTS

The present invention is of compounds that are not polynucleotides yet which bind to complementary DNA and RNA sequences, the compounds according to the present invention include naturally occurring nucleobases or other nucleobases binding moieties (also referred herein as nucleobase analogs) covalently bound to a poly(ether-thioether), a poly(ether-sulfoxide) and/or a poly(ether-sulfone) backbone, which can be used as oligonucleotide analogs in, for example, antisense applications and procedures. The oligonucleotide analogs according to the present invention include a new acyclic biopolymer backbone which best fulfills the six criteria for selecting antisense oligonucleotide analogs listed in the Background section above.

The synthesis, structure and mode of operation of antisense oligonucleotide analogs according to the present invention may be better understood with reference to the drawings and accompanying descriptions.

The polyether polyethylene glycol (PEG) is one of the best biocompatible polymers known, which possesses an array of useful properties. Among them, is a wide range of solubilities in both organic and aqueous media (Mutter et al. (1979) The Peptides Academic Press, 285), lack of toxicity and immunogenicity (Dreborg et al. (1990), Crit. Rev. Ther. Drug Carrier Syst. 6:315), nonbiodegradability, and ease of excretion from living organisms (Yamaoka et al. (1994) J. Pharm. Sci. 83:601).

During the last two decades PEG was used extensively as a covalent modifier of a variety of substrates, producing conjugates which combine some of the properties of both the starting substrate and the polymer. See, Harris, J. M. (1992), Poly(ethylene glycol) Chemistry, Plenum Press, New York. The overwhelming majority of work in this area was prompted by a desire to alter one or more properties of a substrate of interest to make it suitable for a particular biological application. As the arsenal of PEG conjugates and their applications have increased it has become apparent that many undesirable effects triggered in vivo by various biological recognition mechanisms can be minimized by covalent modifications with PEG.

For example, using PEG conjugates, immunogenicity and antigenicity of proteins can be decreased. To this effect see U.S. Pat. No. 4,179,337 to Davis et al. Thrombogenicity as well as cell and protein adherence can be reduced in the case of PEG-grafted surfaces. To this effect see Merrill (1992) Poly(ethylene Glycol) Chemistry, page 199, Plenum Press, Mew York. These beneficial properties conveyed by PEG are of enormous importance for any system requiring blood contact. For further information concerning the biocompatibility of PEG, the reader is referred to Zalipski (1995) Functionalized poly(ethylene glycol) for preparation of biologically relevant conjuoates. Bioconjugate Chem. 6:150. However, all so far known PEG conjugates are exoconjugates, wherein the conjugated moiety is conjugated at one of the terminal hydroxyl groups of PEG (see formula I below).

Due to its biocompatible properties, PEG is used, according to a preferred embodiment of the present invention, as a part of the backbone to which nucleobases, nucleobase analogs (i.e., nucleobase binding moieties) and/or other chemical groups that interact with nucleic acids (e.g., DNA interchelators) are covalently linked to form oligonucleotide analogs having desired characteristics, as is further detailed below.

In U.S. Pat. 5,908,845, a monomeric building block of, for example, the following structural form is described:

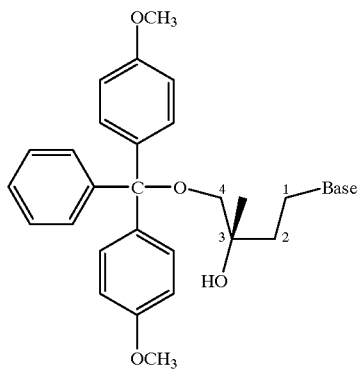

However, synthesis involving this monomeric compound resulted in less than desirable yields. This could be due to the steric hindrance surrounding the chiral center of the compound, resulting from bulky protecting group (such as dimethoxytrityl) and the nucleobase attached to the polyether backbone. Additionally, the secondary nature of the hydroxyl group, may render this hydroxyl group a less efficient nucleophile.

Thus, according to the teachings of the present invention, there is provided a new monomeric compound, in which a sulfhydryl (—SH) group, is utilized as the nucleophile for chain assembly. Sulfhydryl is known as a powerful nucleophile, capable of forming a thioether linkage by substituting a variety of leaving groups, such as halides, tosylates and mesylates, with higher efficiency than a hydroxyl group. The monomeric building block according to the present invention may be thus represented, for example, by the following structural form:

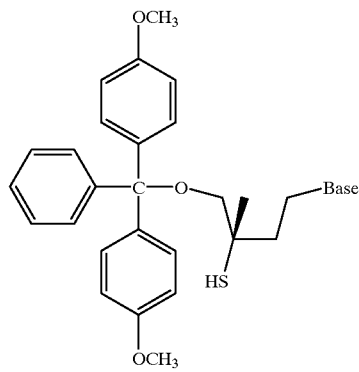

A chain assembled from this novel building block, thus possesses alternating etheric and thioetheric linkages, resulting in, for example, the following poly(ether-thioether) nucleic acid:

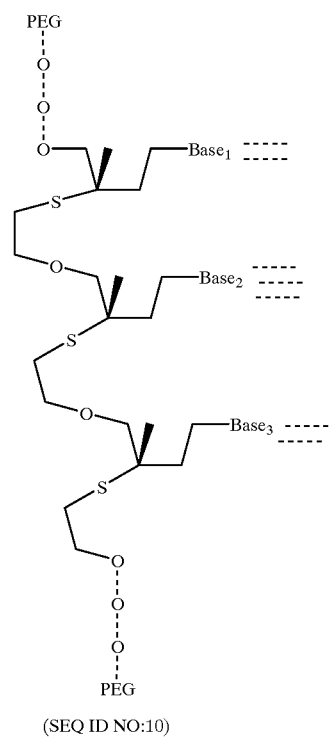

(SEQ ID NO:10)

which, as is further detailed hereinunder, can be oxidized into poly(ether-sulfoxide) and/or poly(ether-sulfone) nucleic acid, which readily interacts with $Mg^{++}$ ions or with other cations, such as, but not limited to, K+, Na+, Zn++ and the like, as is shown below (SEQ ID NOs:11–14).

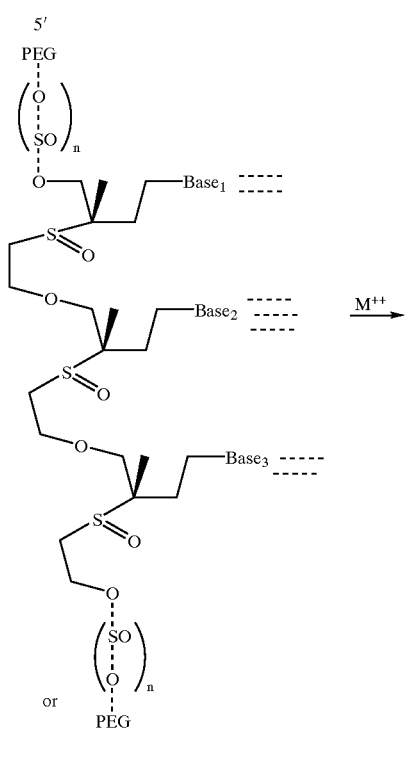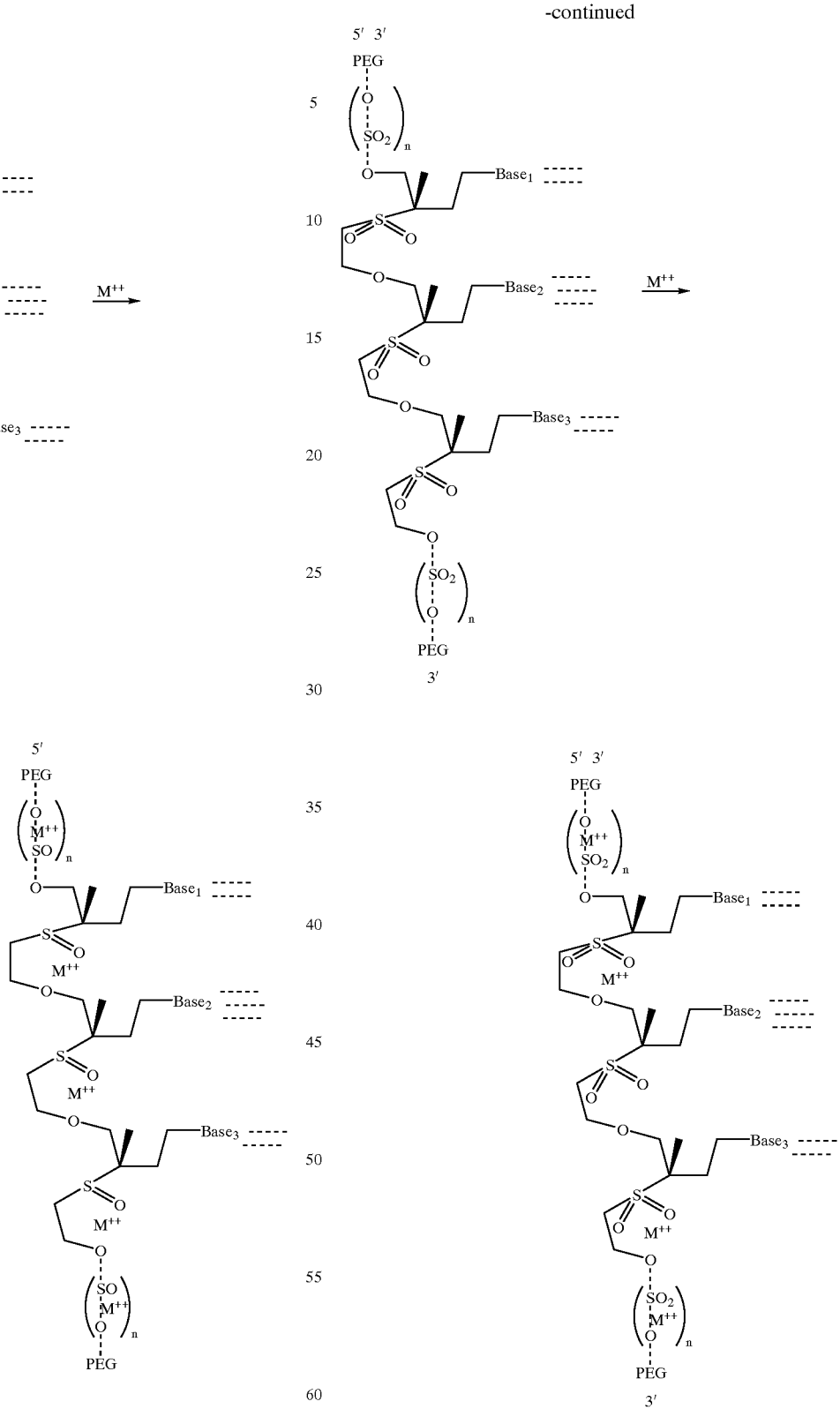

Thus, in the broad sense, the present invention provides a new class of acyclic backbone DNA compounds, that complementarily bind single-stranded (ss) DNA and RNA strands. These compounds are herein referred to as poly (ether-thioether), poly(ether-sulfoxide) or poly(ether-sulfone) nucleic acids. The compounds of the invention generally include (i) a backbone consisting of only C—C, C—S and C—O bonds; and (ii) chemical functionality -continued

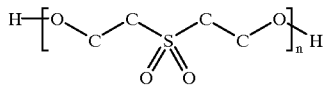

(C)

In one embodiment of the invention, the thioated-PEG nucleic acid compound according to the present invention has the general formula:

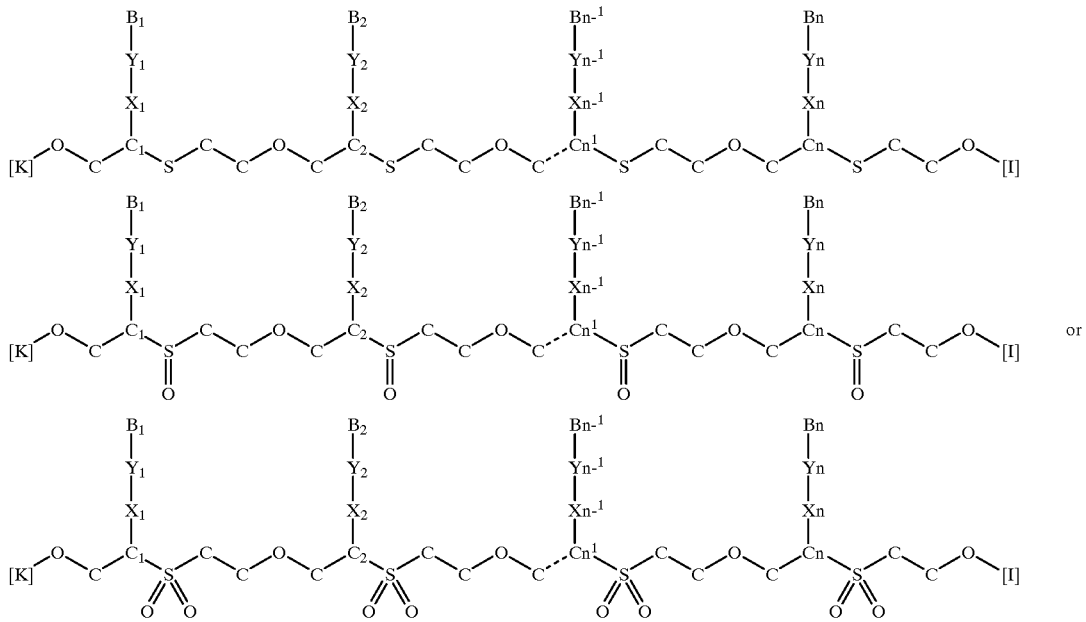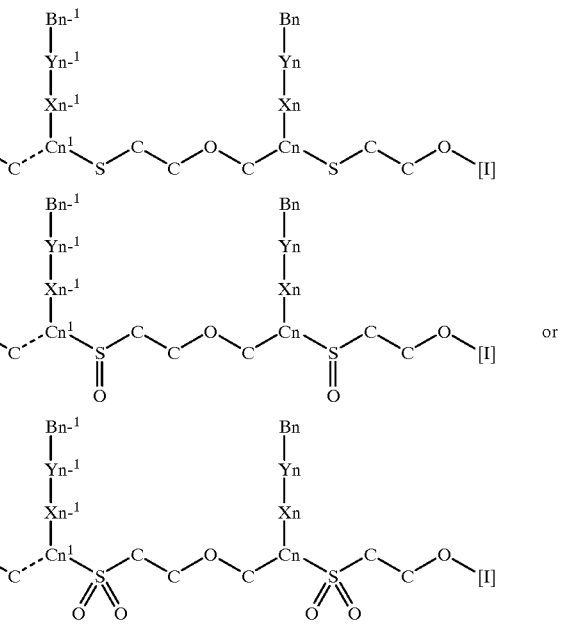

groups, at least some of which are capable of forming suitable hydrogen bonds in a complementary manner with ssDNA and RNA. Representatives chemical functionality groups include either the five naturally occurring DNA and RNA nucleobases, i.e., thymine, adenine, cytosine, uracil or guanine, or modified bases, such as, but not limited to, inosine, thiouracil, bromothymine, azaguanines, azaadenines, 5-methylcytosine, typically attached to a poly (ether-thioether) poly(ether-sulfoxide) and/or poly(ether-sulfone) backbone via a suitable linker arm made of one or more linker groups, such that, in a preferred embodiment of the invention, adjacent chemical functionality groups are separated from one another by eleven atoms, mimicking the polyether nucleic acids of U.S. Pat. No. 5,908,845 and of native DNA.

A thioated-PEG according to the present invention is of the formula:

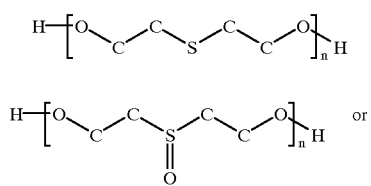

(SEQ ID NOs:4–6) wherein, each of Bl–Bn is a chemical functionality group; each of Yl–Yn is a first linker group; each of Xl–Xn is a second linker group; Cl–Cn are chiral carbon atoms; and [K] and [I] are a first and second exoconjugates.

According to a preferred embodiment of the invention, the chemical functionality groups Bl–Bn are naturally occurring or analog nucleobases attached to the backbone in a predetermined selected order, forming a sequence. Preferably the nucleobases are attached to Y via the position found in nature, i.e., position 9 for purines (e.g., adenine and guanine), and position 1 for pyrimidines (e.g., uracil, thymine and cytosine).

In addition, for various purposes, some of the chemical functionality groups Bl–Bn may be a hydroxy group, an amino group, an amido group, a sulfhydryl group, a carboxylic group, a (C1–C3) alkanoyl group, an aromatic group, a heterocyclic group, a chelating agent (e.g., EDDTA, EGTA, a diol group such as a vicinal diol group, a triol group and the like).

In order to improve binding both to double-stranded and single-stranded DNA, some Bl–Bn functionality groups may be a DNA interchelator such as but not limited to an antraquinone group and the like.

Furthermore, one or more of the functionality groups Bl–Bn may include a reporter molecule such as, for example, a fluorophor, a radioactive label, a chemiluminescent agent, an enzyme, a substrate, a receptor, a ligand, a hapten, an antibody and the like, such that the compound may serve as a labeled or detectable probe in hybridization assays.

Yet furthermore, any one or more of the Bl–Bn chemical functionality groups can be a ligand capable of interacting and covalently alter a complementary DNA or RNA strand. Suitable ligands include natural or analog nucleobase modified with an alkylating electrophile, such as but not limited to 3-(iodoacetamido)propyl, at position 5 of deoxyuridine. In the later case, the modified compound, may upon base pairing with a complementary target nucleic acid strand, to covalently cross link with the 7-position of a guanine residue present in the complementary DNA or RNA strands. Subsequently depurination of the cross-linked guanine and strand scission of the complementary strand may naturally occur under in vivo conditions. To this effect the reader is referred to Meyer et al. (1989) Efficient specific cross-linking and cleavage of DNA by stable synthetic complementary oligodeoxynucleotides. J. Am. Chem. Soc. 111:8517.

Each of Yl–Yn first linker groups can be an alkyl group such as a secondary carbon atom, a tertiary carbon atom or a phosphate group. Preferably, each of the Yl–Yn linker groups is a methylene group or a C-alkanoyl group. Furthermore, each of the Yl–Yn linker groups can be a (C2–C4) alkylene chain or a (C2–C4) alkylene chain substituted with $R_1R_2$. In some cases Y can be just a single bond.

Each of the Xl–Xn second linker groups can be a methylene group (or carbon atom substituted with alkyl groups as $R_1R_2$), an amino group, an amido group, a sulfur atom, an oxygen atom, a selenium atom, a C-alkanoyl group, a phosphate derivative group (e.g. methyl phosphate and phosphoamidate), or preferably a carbonyl group. In some cases X can be just a single bond.

With reference now to FIGS. 1a–b, in accordance with the teachings of the present invention, the X and Y groups serve as linker arms to ensure the presence of preferably eleven atoms spacing between adjacent chemical functionality groups B, as is the case in natural nucleic acids (SEQ ID NOs:15 and 16). FIGS. 1a–b present two adjacent nucleobases (B) on a DNA strand (FIG. 1a) and on a polyether nucleic acid strand according to the preferred embodiment of the present invention (FIG. 1b). Cl–Cn are chiral carbon atoms. The chirality of these atoms may be selected either of S or R configurations. Presently, the R configuration is preferred. As is further detailed hereinbelow, the compound according to the invention is built in a stepwise manner, wherein each monomer or building block is sequentially added to a growing polymer. Therefore, provided that the building blocks can be prepared with a desired chirality (i.e., R or S configurations) a compound of predetermined yet mixed S and R configurations Cl–Cn chiral carbons can be prepared.

Further according to the invention, [K] and [I] are a first and second exoconjugates such as, but not limited to, a polyethylene glycol (PEG) moieties each having one or more repeat units or a hydrogen atom. Exoconjugate [K] and [I] may be water-soluble or water insoluble polymers. Such conjugates can be used to modulate the ability of the compound to cross cell membranes. Nevertheless, any one or both [K] and [I] may be a hydrogen atom.

A preferred thioated-PEG nucleic acid molecule according to the invention have the general formula:

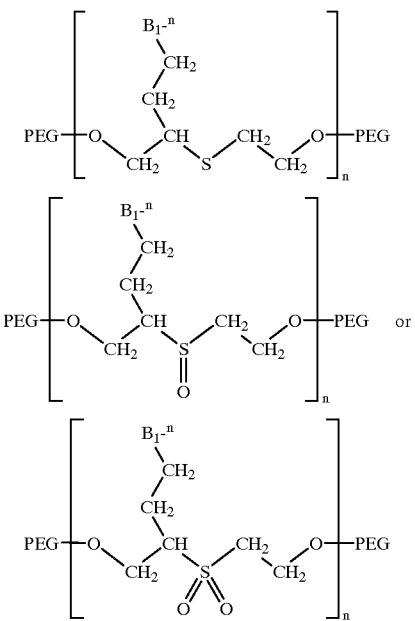

wherein, each of Bl–Bn is a chemical functionality group such as a natural nucleobase or a nucleobase analog and PEG is polyethylene glycol.

Presently, the most preferred embodiment is the compound having the above general formula, wherein B is a natural nucleobase, i.e., thymine (T), adenine (A), cytosine (C), guanine (G) and uracil (U), and wherein n is an integer in the range of 4 to 50, preferably in the range of 8 to 30, most preferably in the range of 12–22.

With reference now to FIG. 2, molecular modeling that represents the hybridization of a prior art tetra-thymidine-polyether nucleic acid compound (SEQ ID NO:17) according to formula III of U.S. Pat. No. 5,908,845 to Segev with natural adenine tetra nucleotide predicts a perfect hybridization match of the hydrogen bonds of the hybrid with minimum energy, wherein O is presented in red; C in yellow; N in blue, P in purple and the hydrogen bonds formed are emphasized by dashed lines, connecting the relevant atoms. It will be appreciated that both sulfur and oxygen reside adjacently in column VI of the periodic table. Indeed, it is not surprising that in many cases an oxygen atom of a molecule is replaceable by a sulfur atom, whereas the thioated analog maintains all or most of the properties of the oxygenated molecule. As is further detailed in the Background section above, this is especially true for thioated oligonucleotides. It is, therefore, anticipated that the poly (ether-thioether) nucleic acid analogs of the present invention behave similarly to the polyether nucleic acids disclosed in U.S. Pat. No. 5,908,845 and in this respect similarly to natural nucleic acids.

This is further emphasized by the molecular modeling of single and double stranded poly(ether-thioether) and poly (ether-sulfone) molecules according to the present invention presented in FIGS. 3–10 (SEQ ID NO:17), wherein Oxygen atoms are shown in red, Carbon atoms in green, Nitrogen atoms in blue, Sulfur atoms in yellow and hydrogen atoms in white.

The poly(ether-thioether), poly(ether-sulfoxide) or poly (ether-sulfone) nucleic acids of the present invention may be synthesized using standard DNA synthesis procedures, either in solution or preferably on a solid phase.

The building blocks used are specially designed chiral, S or R monomers, or their activated forms.

The monomer building blocks according to the invention arc the general formula:

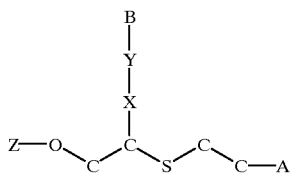

wherein B, Y and X are as defined above; Z is a suitable protecting group; and A is a suitable leaving group.

Should a specific building block include B which is a natlral or analog nucleobase, the amino groups thereof may be protected with any conventional protecting group, such as, but not limited to, a methylbenzyl cthcr, a benzamido group, an isobutyramido group, a t-butoxycarbonyl (Boc) group, a fluorenylmethyloxycarbonyl (Fmoc) group and the like.

Z is a protecting group for protecting the terminal hydroxyl group of the monomer. Z can be any suitable protecting group known in the art, such as but not limited to a dimethoxytrityl group, a trityl group, a monomethoxytrityl group or a silyl group. Preferably Z is a dimethoxytrityl group.

A is a leaving group such as a halide group, a sulfonate group, such as methane- or p-methylphenyl sulfonate, an ammonium derivative, or any radical moiety that could be replaced by SN1 or SN2 mechanisms including the well known Mitsunobu Reaction (see, Mitsunobu. O., Synthesis, 1981,1)

A preferred monomer building block according to the invention have the general formula:

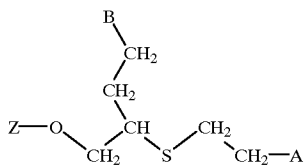

wherein, B, Z and A are as defined above.

This monomer is condensed sequentially to a polymeric support such as a controlled pore glass or derivatized polystyrene and the like, which includes an exposed reactive chemical group such as hydroxyl, amino, thiol, phosphorous and the like which interact with the carbon atom adjacent leaving group A, causing the group to leave. The addition of an appropriate bases is performed by a cycle which includes (a) condensing the polymeric support with the monomer by activating molecules; (b) capping and thereby inactivating unreacted reactive groups on the polymeric support; and (c) deprotecting the Z group to thereby expose a free hydroxyl group. This completes the first cycle. In subsequent cycles free hydroxyl groups are condensed with subsequent monomers having B groups of a desired nature to thereby obtain a poly(ether-thioether) molecule of a desired sequence. Following the last cycle, PEG may be condensed to the free hydroxyl group of the terminal monomer, using a similar condensation approach used for cycling.

For the preparation a poly(ether-sulfoxide) nucleic acid, the product resulting from the above procedure is oxidized with an oxidizing agent, preferably with 1.2 equivalents of meta-chloro perbenzoic acid.

For the preparation a poly(ether-sulfone) nucleic acid, the product resulting from the above procedure is oxidized with another, more prominent, oxidizing agent, preferably with 4-methylmorpholine N-oxide.

Release of the polymeric product from the polymeric support may be achieved under basic conditions, such as in the presence of ammonium hydroxide, or another base, or with any other suitable reagent depending on the nature of attachment to the polymeric support.

In a preferred embodiment of the invention a poly(ether-thioether), poly(ether-sulfoxide) or poly(ether-sulfone) nucleic acid according to any of the embodiments described hereinabove is interacted with ions of an alkaline metal such as but not limited to $Na^+$, earth alkaline metal such as but not limited to $Ca^{++}$ and $Mg^{++}$, or ions of a transition metal such as, but not limited to, $K^+$, $Fe^{++}$, $Zn^{++}$, $Cu^{++}$, $Mn^{++}$ and $Cr^{++}$, capable of forming coordinative or other bonds with oxygen atoms or other electronegative moieties of the poly(ether-thioether), poly(ether-sulfoxide) or poly(ether-sulfone) backbone and/or the linker groups. Such coordinative bonds may assist in bringing the poly(ether-thioether), poly(ether-sulfoxide) or poly(ether-sulfone) nucleic acids according to the invention to a conformation highly suitable for base pairing with a complementary single-stranded DNA or RNA.

The present invention is further directed at use of poly(ether-thioether), poly(ether-sulfoxide) or poly(ether-sulfone) nucleic acids molecules in solid-phase biochemistry (see, Solid-Phase Biochemistry—Analytical and Synthetic Aspects (1983) W. H. Scouten, ed., John Wiley & Sons, New York), notably solid-phase biosystems, especially bioassays or solid-phase techniques which concerns diagnostic detection/quantitation or affinity purification of complementary nucleic acids (see, Affinity Chromatography—A Practical Approach (1986) P. D. G. Dean, W. S. Johnson and F. A. Middle, eds., IRL Press Ltd., Oxford; Nucleic Acid Hybridization—A Practical Approach (1987) B. D. Harnes and S. J. Higgins, IRL Press Ltd., Oxford).

Present day methods for performing such bioassays or purification techniques almost exclusively utilize "normal" or slightly modified oligonucleotides, either physically adsorbed or bound through a substantially permanent covalent anchoring linkage to solid supports such as cellulose, glass beads, including those with controlled porosity (Mizutani, et al. (1986) J. Chromatogr. 356:202), "Sepharose", "Sephadex", polyacrylamide, agarose, hydroxyalkyl methacrylate gels, porous particulate alumina, porous ceramics, diobonded silica, or contiguous materials such as filter discs of nylon or nitrocellulose. One example employs the chemical synthesis of oligo-dT on cellulose beads for the affinity isolation of poly A tail containing mRNA (Gilham in Methods in Enzymology (1971) L. Grossmann and K. Moldave, eds., vol. 21, part D, page 191, Academic Press, New York and London).

All the above-mentioned methods are applicable within the context of the present invention. However, when possible. covalent linkage is preferred over the physical adsorption of the molecules in question, since the latter approach has the disadvantage that some of the immobilized molecules can be washed out (desorbed) during the hybridization or affinity process.

There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight.

Thus, poly(ether-thioether), poly(ether-sulfoxide) or poly(ether-sulfone) nucleic acids species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They can therefore replace common oligonucleotides in hybridization assays such as but not limited to blot hybridizations ("Southern" and "Northern"), dot blot hybridizations, reverse blot hybridizations, in situ hybridizations, liquid phase hybridizations, clones (bacteria/phages, etc.) screening and in other assays involving hybridizations such as but not limited to PCR, sequencing, primer extension and the like.

They also can be loaded onto solid supports in large amounts, thus further increasing the sensitivity/capacity of the solid-phase technique. Further, certain types of studies concerning the use of poly(ether-thioether), poly(ether-sulfoxide) or poly(ether-sulfone) nucleic acids in solid-phase biochemistry can be approached, facilitated, or greatly accelerated by use of the recently-reported "light-directed, spatially addressable, parallel chemical synthesis" technology (Fodor, et al. (1991) Science, 251:767), a technique that combines solid-phase chemistry and photolithography to produce thousands of highly diverse, but identifiable, permanently immobilized compounds (such as proteins) in a substantially simultaneous way.

The present invention is further directed at therapeutic and/or prophylactic uses for poly(ether-thioether), poly(ether-sulfoxide) or poly(ether-sulfone) nucleic acids. Likely therapeutic and prophylactic targets according to the invention include but are not limited to human papillomavirus (HPV), herpes simplex virus (HSV), candida albicans, influenza virus, human lo immunodeficiency virus (HIV), intracellular adhesion molecules (ICAM), cytomegalovirus (CMV), phospholipase A2 (PLA2), 5-lipoxygenase (5-LO), protein kinase C (PKC), and RAS oncogene.

Potential applications of such targeting include, but are not limited to, treatments for labial, ocular and cervical cancer, genital warts, Kaposi's sarcoma, common warts, skin and systemic fungal infections, AIDS, pneumonia, flu, mononucleosis, retinitis and pneumonitis in immunosuppressed patients, ocular, skin and systemic inflammation, cancer, cardiovascular disease, psoriasis, asthma, cardiac infarction, cardiovascular collapse, kidney disease, gastrointestinal disease, osteoarthritis, rheumatoid arthritis, septic shock, acute pancreatitis, and Crohn's disease.

For therapeutic or prophylactic treatment, the poly(ether-thioether), poly(ether-sulfoxide) or poly(ether-sulfone) nucleic acids of the present invention can be formulated in a pharmaceutical composition, which may include thickeners, carriers, buffers, diluents, surface active agents. preservatives, and the like, all as well known in the art. Pharmaceutical compositions may also include one or more active ingredients such as but not limited to antiinflammatory agents, antimicrobial agents, and the like in addition to poly(ether-thioether), poly(ether-sulfoxide) or poly(ether-sulfone) nucleic acids.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions, which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Treatments of this type can be practiced on a variety of organisms ranging from unicellular prokaryotic and eukaryotic organisms to multicellular eukaryotic organisms. Any organism that utilizes transcription (including DNA-RNA transcription and reverse transcription), RNA transcripts or RNA-protein translation as a fundamental part of its hereditary, metabolic or cellular control is susceptible to therapeutic and/or prophylactic treatment in accordance with the present invention. Seemingly diverse organisms such as yeast, bacteria, algae, protozoa, all plants and all higher animal forms, including warm-blooded animals, can be treated.

Further, each cell of multicellular eukaryotes can be treated since they include both DNA-RNA transcription and RNA-protein translation as integral parts of their cellular activity.

Furthermore, many of the organelles (e.g., mitochondria, chloroplasts and chromoplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

Poly(ether-thioether), poly(ether-sulfoxide) or poly(ether-sulfone) nucleic acids according to the present invention enjoy various advantages over existing oligonucleotide analog technologies.

First, according to a preferred embodiment of the invention, the poly(ether-thioether), poly(ether-sulfoxide) or poly(ether-sulfone) nucleic acids' backbone is thioated-or sulfonated PEG known to be soluble both in aqueous and in organic solvents, in high concentrations. The poly(ether-thioether), poly(ether-sulfoxide) or poly(ether-sulfone) backbone of poly(ether-thioether), poly(ether-sulfoxide) or poly(ether-sulfone) nucleic acids according to the invention possess hydrophobicity on one hand and solubility in water on the other. This unique characteristic of poly(ether-thioether), poly(ether-sulfoxide) or poly(ether-sulfone) nucleic acids enables a balanced hybridization between poly(ether-thioether), poly(ether-sulfoxide) or poly(ether-sulfone) nucleic acids and complementary DNA or RNA molecules, as poly(ether-thioether), poly(ether-sulfoxide) or poly(ether-sulfone) nucleic acids do not interact too strong with complementary sequences as protein nucleic acids (PNAs) do, yet poly(ether-thioether), poly(ether-sulfoxide) or poly(ether-sulfone) nucleic acids are not highly solvated in aqueous media as native DNA and RNA strands.

Second, one of the major drawbacks of PNAs when used as antisense molecules is that PNA-DNA hybrids are characterized by high melting temperature (Tm). For example, the Tm value for a duplex such as PNA-$T_{10}$–$dA_{10}$ is greater than 70° C., whereas the Tm value of the equivalent native double stranded DNA ($dT_{10}$–$dA_{10}$) (SEQ ID NO:18) is nearly three fold lower, about 24° C. Because PNAs bind complementary sequences so strongly, at body temperature (e.g., 37° C.) PNAs lack the specificity to their intended counterparts and end up binding not just to target sequences but also to other strands of DNA, RNA, or even proteins, incapacitating the cell in unforeseen ways. PNAs act as a micelle when the lysine residues are solvated. PNAs are poorly miscible in water, while the hydrophobic nature of the backbone have a tendency to seek for a nonpolar environment e.g., the bases of the natural complementary DNA. These hydrophobic interactions are the major driving force for the formation of highly stable PNA-DNA hybrid and therefore very high Tm values for such hybrids. The unique solubility nature of poly(ether-thioether), poly(ether-sulfoxide) or poly(ether-sulfone) nucleic acids, by conserving the hydrophobic-hydrophilic properties of polyethers such as PEG, yield Tm values slightly higher than natural DNA, yet much lower values than PNAs, which moderate values are of great importance for specificity.

Third, polyether based compounds, such as cyclodextrins, have a tendency to form helices, which are stabilized in solution by water and metal ions under physiological conditions. This characteristic of polyether based compounds renders these compounds highly suitable acyclic backbones for nucleobases to be base paired with complementary DNA or RNA molecules.

Fourth, PEG is approved by the FDA for parenteral use, topical application, and as a constituent of suppositories, nasal sprays, foods and cosmetics. PEG is of low toxicity when administered orally or parenterally, and only large quantities involve adverse reactions. See, Smyth, H. F. et al. (1955) J. Am. Pharm. Assoc., 34:27. Evidences accumulated experiencing administration of PEG-protein conjugates, suggest that both the plasma half-lives (circulating time) of PEG conjugated proteins and their bioavailability improves as compared with the native proteins, which improvement is accompanied by improved efficacy. Ganser et al. (1989) Blood, 73:31, observed less side effects at lower dosage using PEG-modifications. Reduced toxicity has been observed with several PEG-modified enzymes, see Fuertges et al. (1990) J. Contr. Release, 11:139. Another advantage in exploiting the improved pharmacokinetics of PEG is the option of administrating bolus injections instead of continuous intravenous infusions, as described by Pizzo (1991) Adv. Drug Del. Rev. 6:153. In the preferred embodiments of the invention, poly(ether-thioether) nucleic acids include a PEG backbone and/or are conjugated to PEG exoconjugates and therefore enjoy the above listed advantages.

Finally, as is further detailed in the Examples section below, poly(ether-thioether), poly(ether-sulfoxide) or poly (ether-sulfone) nucleic acids synthesis preferably involves using monomers having one chiral center with known chirality, or an R/S, e.g. racemic, mixture of R and S monomers. This monomer, which is presented hereinabove, is condensed as much as needed to prepare the appropriate oligonucleotide having a poly(ether-thioether) backbone and a preselected and desirable nucleobases sequence. During these condensations, the chiral center is not susceptible to racemization. As is further detailed in the Examples section hereinbelow, the synthesis of the monomers involves a chiral starting material, which is available in a chirality in a pure form. In contrast, Miller et al. (1971) J. Am. Chem. Soc. 93:6657, has prepared non-ionic oligonucleotide analogs, in which the hydroxyl group in the phosphate moiety is replaced by a methyl group to yield methylphosphonate linkages. As shown by Miller, each methylphosphonate linkage (p) may have an R or an S chiral configuration. Thus for example, dApA(S)(dA)$_{12}$ (SEQ ID NO:19) hybridized to poly dT has a Tm value higher by 4.4° C. as compared with dApA(R)(dA)$_{12}$ (SEQ ID NO:20). This observation suggests that the methyl groups in the R configuration may provide some specific steric hindrance. Since there is an equal chance per each synthesis step for R or S configurations, which decreases dramatically the Tm, introduction of more than four methylphosphonates in an oligonucleotide chain typically results in Ca. 20° C. decrease in Tm values. Obviously, it is impossible to separate between the diastereoisomers formed in each step of synthesis. The same argumentation is for the replacement of hydroxyl groups with sulfhydryl groups in the phosphate moiety as in phosphothioate oligonucleotide analogs. Furthermore, these materials are sparingly soluble in water. The solubility of this family of compounds in aqueous buffers depends on the size, composition and possibly even the sequence of the oligomer. A high percentage of guanine, or even worse, an aggregate of contiguous guanine residues, sharply reduces the solubility of such compounds. For example, d(CpT)$_8$ (SEQ ID NO:21) is soluble up to millimolar concentrations, whereas d(ApG)$_8$ (SEQ ID NO:22) has solubility of less than 0.1 mM.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE 1

Synthesis of R/S Monomers for Synthesizing Poly (ether-thioether) Nucleic Acids According to the Present Invention Preparation of a Monomer Described by Formula Q The starting material for synthesizing a monomer according to preferred embodiments of the present invention described above, in which the linker groups are both methylene, is methyl 4-bromocrotonate. This route of syntheses results in a R/S isomer mixture of formula Q, at the chiral center C*. Additional consecutive synthesis steps are based upon the following:

Preparation of methyl 4-hydroxycrotonate (Compound A) by bromide substitution

To a well-stirred mixture of silver oxide (11.6 grams, 0.05 mol) in 195 ml of water, methyl 4-bromocrotonate (17.9 grams, 0.1 mol) was added. The mixture was stirred for 24 hours at 25° C. and then heated for additional 6 hours at 60° C. Following filtration, water was evaporated under reduced pressure, resulting in a liquid residue which was further distilled under vacuum. Compound A, as a clear liquid, was obtained (6 grams, 0.3 mmol, 51% yield) having a boiling point of 77–80° C.; NMR (CDCl$_3$): 3.65 (s, 3H), 4.8 (s, 3H), 6.0 (m, 1H), 7.0 (m, 1H).

This process is briefly described by:

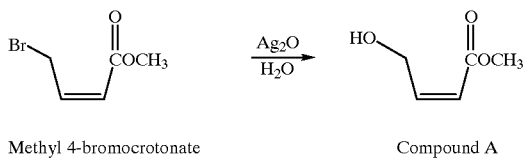

Methyl 4-bromocrotonate          Compound A

Preparation of methyl 4(4,4'-Dimethoxytrityl) crotonate (Compound B)

A mixture of methyl-4-hydroxycrotonate (Compound A) (11.6 grams, 100 mmoles) was co-evaporated with dry pyridine and was thereafter dissolved in 200 ml of same. The mixture obtained was cooled in an ice-water bath, and 40.6 grams (120 mmoles) of dimethoxytrityl chloride (Aldrich), dissolved in 100 ml of dry pyridine, was added dropwise. The mixture was kept at room temperature for 17 hours, after which the mixture was evaporated to dryness and extracted with 500 ml ethylacetate/500 ml water, washed once with 100 ml saturated $NaHCO_3$ solution, twice with water and twice with brine solution. The obtained organic layer was dried over anhydrous sodium sulfate, evaporated and purified by column chromatography using hexane/ethylacetate (2/1), 0.5% pyridine. The resulting Compound B (40.2 grams, 96% yield) migrated with Rf=0.84. NMR ($CDCl_3$): 3.69 (s, 3H), 3.70 (m, 2H), 3.77 (s, 6H), 6.1 (m, 1H), 6.87.55 (m, 13H), 7.05 (m, 1H).

This process is briefly described by:

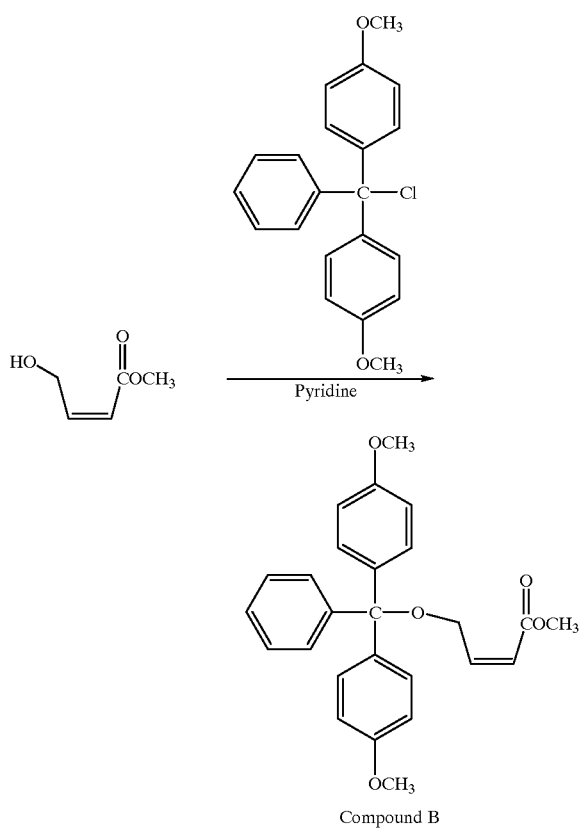

Compound B

Preparation of methyl 3-thioethanol 4-(4,4'dimethoxytrityl) crotonate (Compound C)

To a solution of Compound B (41.8 grams, 100 mmoles) in 500 ml methanol and 20 grams of potassium carbonate, mercaptoethanol (Aldrich, 15.62 grams, 200 mmoles) was added in bulk. The reaction mixture was stirred at room temperature for 8 hours. The solvent was evaporated, and the residue was extracted with 500 ml ethylacetate/500 ml water, washed twice with water and twice with brine solution. The obtained organic layer was dried over anhydrous sodium sulfate, evaporated and purified by column chromatography using hexane/ethylacetate (2/1), 0.5% pyridine. The resulting R/S mixture of Compound C (49 grams, essentially 100% yield) migrated with Rf=0.2. NMR ($CDCl_3$): [2.42 and 2.94] (m, 2H), 2.61 (t, 2H), 3.14 (m, 2H), 3.30 (m, 1H), 3.65 (m, 3H), 3.7 (s, 3H), 3.79 (s, 6H), 6.81–7.44 (m, 13H).

This process is briefly described by:

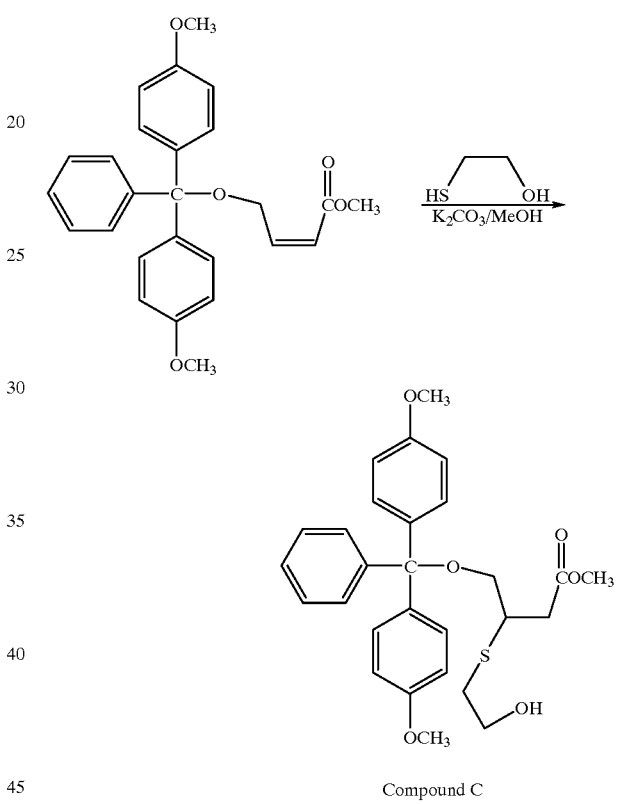

Compound C

Preparation of methyl 3-thioethyl (t-butyldimethylsilyl ether), 4-(4,4'-dimethoxytrityl)-butylate (Compound D)

To a solution of compound C (4.96 grams, 10 mmoles) and of imidazole (Aldrich, 1.7 grams, 25 mmoles) in 100 ml of dichloromethane, a solution of t-butyldimethylsilyl chloride (1.8 grams, 12 mmoles) in 50 ml of dichloromethane was added dropwise at room temperature. After stirring for 2 hours, the solvent was evaporated to dryness, and the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ethylacetate (2/1), 0.5% pyridine. The resulting R/S mixture of Compound D (5.82 grams, 95% yield) migrated with Rf=0.62. NMR ($CDCl_3$): 0.50 (s, 6H), 0.89 (s, 9H), [2.38 and 2.83] (m, 2H), 2.59 (m, 2H), 3.30 (m, 1H), 3.11–3.15 (m, 2H), 3.66 (s, 3H), 3.69 (m, 2H), 3.79 (s, 6H), 6.80–7.44 (m, 13H).

This process is briefly described by:

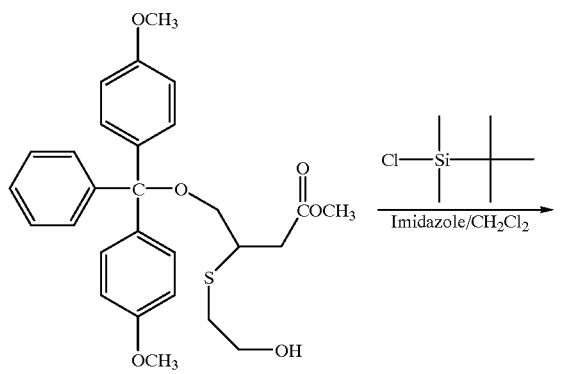

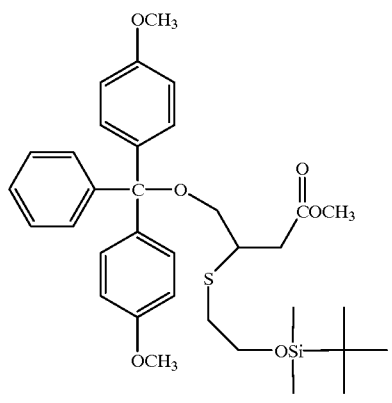

Compound D

Preparation of 3-thioethyl (t-butyldimethylsilyl ether), 4-(4,4'-dimethoxytrityl)-1-butanol (Compound E)

To a solution of Compound D (6.1 grams, 10 mmoles) in 300 ml dry tetrahydrofuran at room temperature LiRH$_4$ (Aldrich, 0.544 grams, 25 mmoles) was added in portions. Ten minutes later, the reaction was refluxed for 10 minutes and methanol (10 ml) was added dropwise to the refluxing solution. Refluxing was maintained for additional 2 hours, after which the solvent was evaporated to dryness, and the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ethylacetate (2/1), 0.5% pyridine. The resulting R/S mixture of Compound E (5.23 grams, 90% yield) migrated with Rf=0.39. NMR (CDCl$_3$): 0.05 (s, 6H), 0.89 (s, 9H), [1.69 and 2.01] (m, 2H), 2.60 (t, 2H), [2.92 and 3.15] (m, 2H), 3.30(m, 1H), 3.69(t, 2H), 3.78 (s, 6H), 6.80–7.45 (m, 13H).

This process is briefly described by:

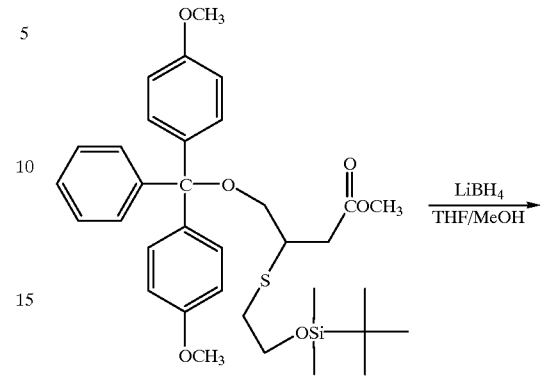

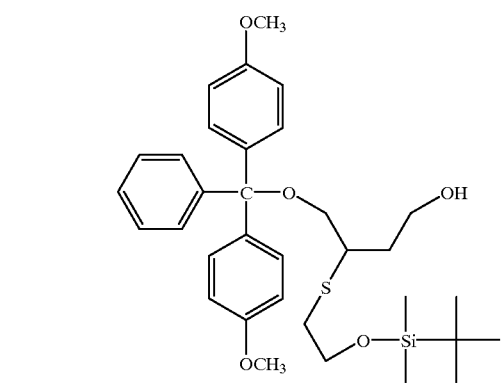

Compound E

Preparation of 1-mesylate, 3-thioethyl (t-butyldimethylsilyl ether), 4-(4,4'-dimethoxytrityl)-1-butane (Compound F)

Compound E (5.82 grams, 10 mmoles) was co-evaporated with dry pyridine, the resulting oil was dissolved in 200 ml of dry pyridine under argon, and cooled to 0° C. To the resulting solution methanesulfonyl chloride was added (928 microliters, 12 mmoles), the reaction mixture was allowed to warm to room temperature and stirred for 3 additional hours, at which point ethanol (2 ml) was added. Following additional 15 minutes of stirring, the solvent was evaporated to dryness, the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ ethylacetate (1/1), 0.5% pyridine. The resulting R/S mixture of Compound F (6.41 grams, 97% yield) migrated with Rf=0.85. NMR (CDCl$_3$): 0.05 (s, 6H), 0.90 (s, 9H), [1.81 and 2.04] (m, 2H), 2.55 (t, 3H), [2.91 and 3.20 (m, 2H), 3.02 (s, 3H), 3.33 (m, 1H), 3.69 (t, 2H), 3.79 (s, 6H), 4.37 (m, 2H), 6.81–7.46 (m, 13H).

This process is briefly described by:

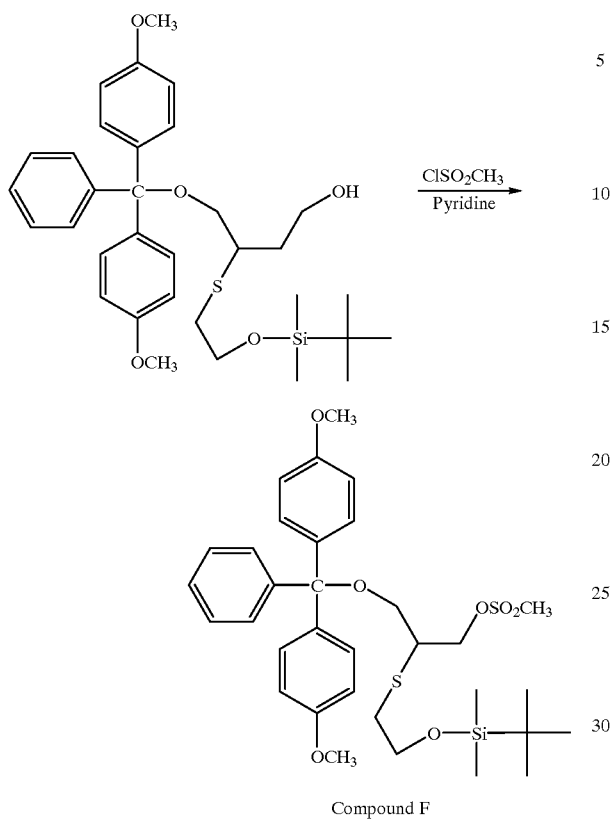

Compound F

This process is briefly described by:

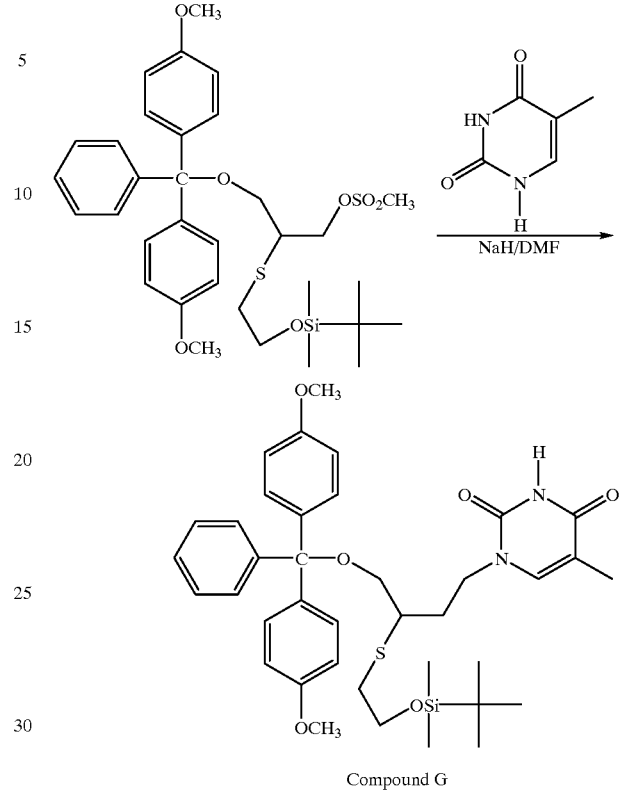

Compound G

Attachment of a Nucleobase to Compound F (Compound G)

Protection of the Thymine Amino Group by N-methylbenzyl Ether (Compound H)

To a solution of thymine (Aldrich, 1.26 grams, 10 mmoles) in 200 ml of dry DMF, was added, in bulk, sodium hydride (480 mgrams, 12 mmoles) as 60% dispersion in mineral oil. The reaction mixture was stirred for 2 hours, at which time the slurry solution became clear. Then, a solution of Compound F (6.6 grams, 10 mmoles) in 50 ml of dry pyridine was added in bulk. The reaction mixture was heated to 110° C. for 18 hours, the solvent was evaporated to dryness, and the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ethylacetate (1/1), 0.5% pyridine. The resulting R/S mixture of Compound G (3.5 grams, 50% yield) migrated with Rf=0.44. NMR (CDCl$_3$): 0.05 (s, 6H), 0.88(s, 9H), [1.65 and 2.25] (m, 2H), 1.89 (s, 3H), 2.57 (t, 2 H), [3.08 and 3.82] (m, 2H), 3.30 (m, 1H), 3.64 (t, 2H), 3.80 (s, 6H), 6.96 (s, 1H), 6.80–7.44 (m, 13H), 8.90 (s, broad, 1H).

To a solution of Compound G (6.9 grams, 10 mmoles) in dry acetonitrile, 1,8-diazabicyclo[5.4.0]undec-7-ene (DBU) (Aldrich, 1.82 grams, 1.5 ml, 12 mmoles) was added, by injection under argon, and benzychloromethyl ether (BOM, Fluka, 1.56 grams, 1.4 ml, 12 mmoles) by injection under argon. The reaction mixture was stirred under argon at room temperature for 18 hours. Additional 20% of DBU and of BOM were added, and the solution was stirred for additional 2 hours at room temperature. The solvent was evaporated to dryness, and the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ethylacetate (3/1), 0.5% pyridine. The resulting R/S mixture of Compound H (7.32 grams, 91% yield), migrated with Rf=0.64. NMR (CDCl$_3$): 0.05 (s, 6H), 0.88(s, 9H), [1.65 and 2.25] (m, 2H), 1.89 (s, 3H), 2.57 (t, 2H), [3.08 and 3.82] (m, 2H), 3.30 (m, 1H), 3.64 (t, 2H), 3.80 (s, 6H), 4.68 (s, 2H), 5.48 (s, 2H), 6.90 (s, 1H), 6.80–7.44 (m, 18H).

This process is briefly described by:

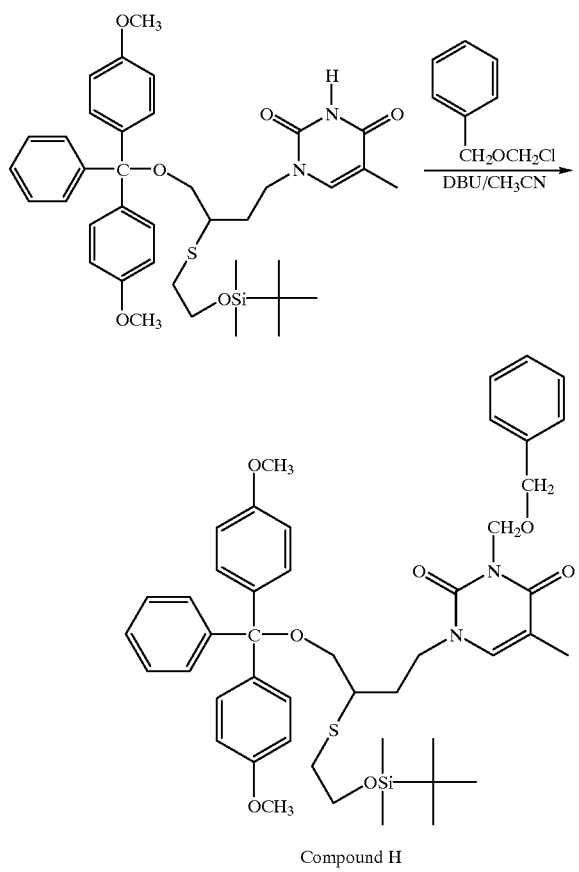

Compound H

Protection of the Thymine Amino Group by Benzoate (Compound H1, an Alternative to Compound H Preparation of 3-N-benzoylthymine This compound is prepared according to the method by Cruickshank et al. published in Tetrahedron Letters (1984) Vol. 25, 681.

This process is briefly described by:

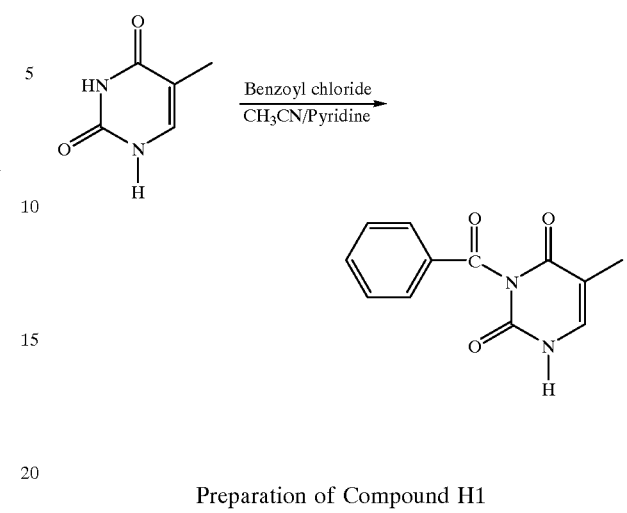

Preparation of Compound H1

To a stirred solution of $N_3$-benzoylthymine (2.35 grams, 10.21 mmol) in dry THF (100 ml) under argon triphenyl phosphine (4.29 grams, 16.37 mmol) and alcohol (4.5 grams, 7.72 mmol) were added at room temperature. After 15 minutes, diethylazodicarboxylate (2.84 grams, 16.32 mmol, 2.57 ml) was added slowly during a 30 minutes time period. The reaction mixture was covered with aluminum foil and allowed to steer at room temperature under argon for 24 hours. The solvent was evaporated to dryness and the residue was dissolved in EtOAc (300 ml). The organic phase was washed with 5% $NaHCO_3$ solution (100 ml), water and brine, and was dried over sodium sulfate. The dried EtOAc extract was evaporated to dryness to give an orange oil, which was purified by column chromatography using hexane/ethylacetate (2/1) and 0.5% pyridine. The resulting Compound H1 (5.25 grams, 85% yield) migrated with Rf=0.38. NMR (CDC13): 0.05 (s, 6H), 0.88 (s,3H), [1.73 and 2.25] (m, 2H), 1.93 (s, 3H), 2.58 (t, 3H), [3.18 and 3.87] (m, 2H), 3.33 (m, 1H), 3.65 (t, 2H), 3.80 (s, 6H), 7.08 (s, 1H), 6.8–7.92 (m, 18H).

This process is briefly described by:

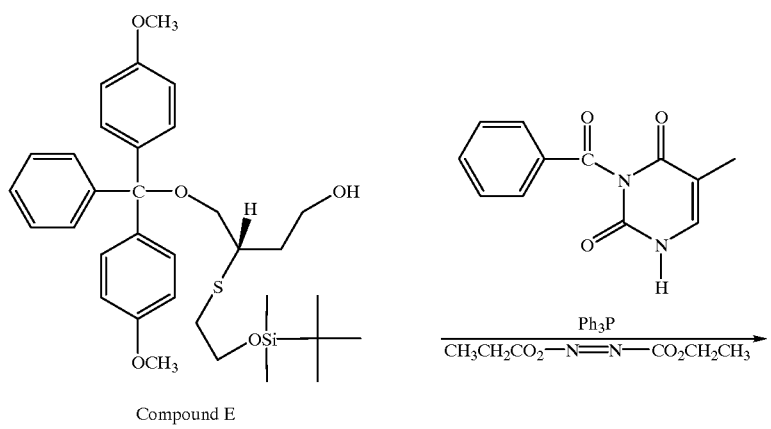

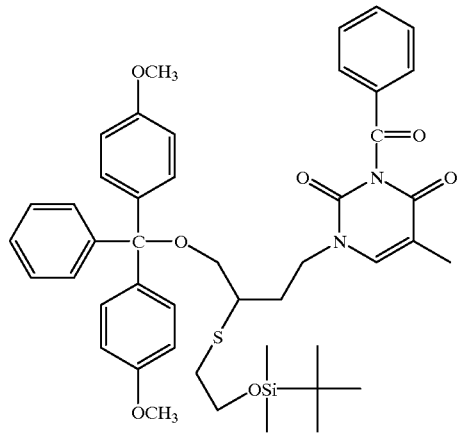

Compound H1

Deprotection of the Hydroxyl t-butyldimethyl Silyl Protecting Group

To a solution of Compound H (7.97 grams, 10 mmoles) (or Compound H1 in the alternative) in 100 ml of tetrahydrofuran, tetrabutylammonium fluoride hydrate (Aldrich, 3.13 grams, 12.0 mmoles) was added, and the reaction mixture was stirred at room temperature for 18 hours. The solvent was then evaporated to dryness, and the residue was extracted with 200 ml of ethylacetate/200 ml water, washed twice with water and twice with brine solution. The obtained organic layer was dried over anhydrous sodium is sulfate, evaporated and purified by silica gel column chromatography using 1% methanol in dichloromethane, 0.5% pyridine. The resulting R/S mixture of Compound I (6.10 grams, 89% yield), migrated with Rf=0.36. NMR (CDCl$_3$): [1.74 and 2.25] (m, 2H), 1.87 (s, 3H), 2.57 (t, 2H), [3.21 and 3.87] (m, 2H), 3.32 (m, 1H), 3.55 (m, 2H), 3.87 (s, 6H), 4.68 (s, 2H), 5.48 (s, 2H), 6.90 (s, 1H), 6.79–7.43 (m, 18H).

This process is briefly described by:

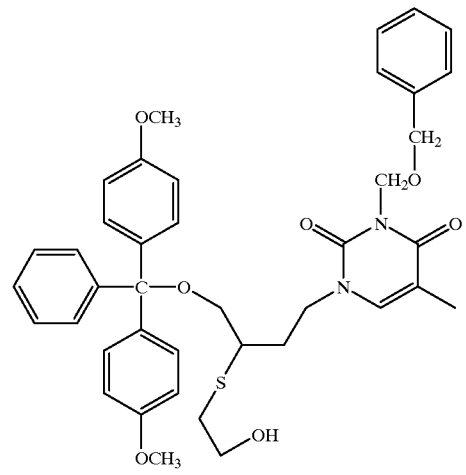

Compound I

Alternatively tetrabutylammonium fluoride is reacted with compound H1 under the same conditions described hereinabove for the preparation of compound I.

This process is briefly described by:

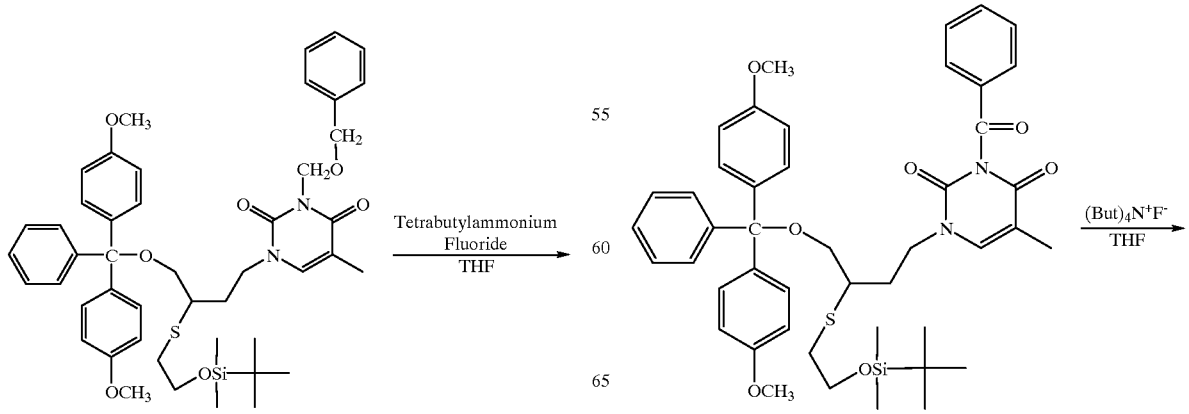

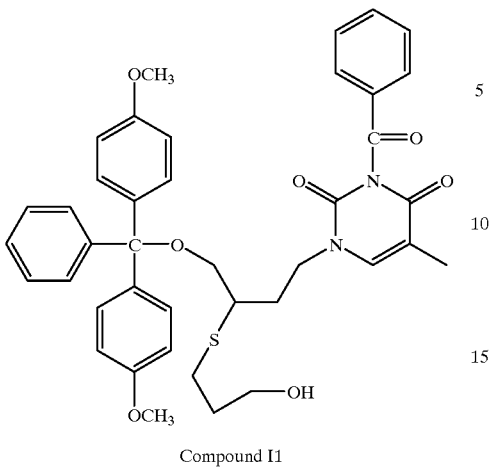

Compound I1

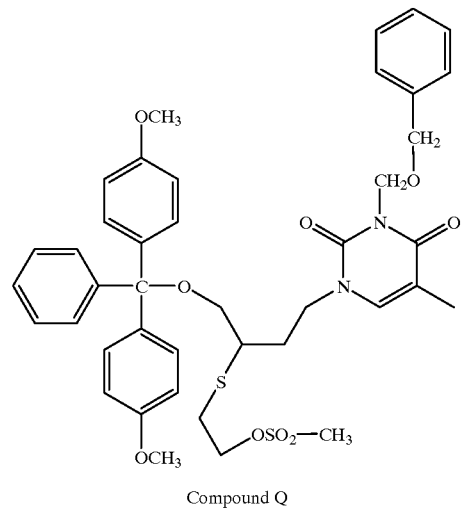

Compound Q

Preparation of Compound Q

To a solution of Compound I (6.96 grams, 10 mmoles) in 100 ml of dry pyridine, which was cooled in an ice water bath, methanesulfonyl chloride (Aldrich, 1.36 grams, 0.94 ml, 12 mmoles) was added by injection under argon. The reaction mixture was stirred at 0° C. for 30 minutes, followed by stirring at room temperature for additional two hours.

The solvent was then evaporated to dryness, and the residue was extracted with 200 ml of ethylacetate/200 ml of 5% sodium bicarbonate solution, washed twice with water and twice with brine solution. The obtained organic layer was dried over anhydrous sodium sulfate, evaporated and to purified by silica gel column chromatography using ethylacetate/hexane (1/1), 0.5% pyridine. The resulting R/S mixture of Compound Q (6.10 grams, 89% yield), migrated with Rf=0.24. NMR (CDCl$_3$): [1.74 and 2.25] (m, 2H), 1.87 (s, 3H), 2.57 (t, 2H), [3.21 and 3.87] (m, 2H), 3.32 (m, 1H), 3.55 (m, 2H), 3.87 (s, 6H), 4.68 (s, 2H), 5.48 (s, 2H), 6.90 (s, 1H), 6.79–7.43 (m, 18H).

This process is briefly described by:

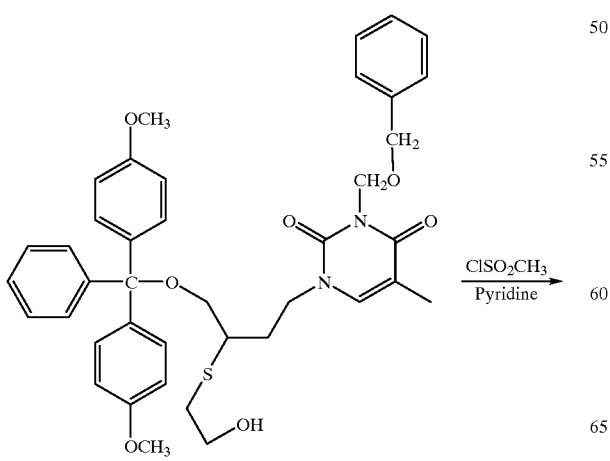

This procedure also applies for the preparation of compound Q 1, briefly described by:

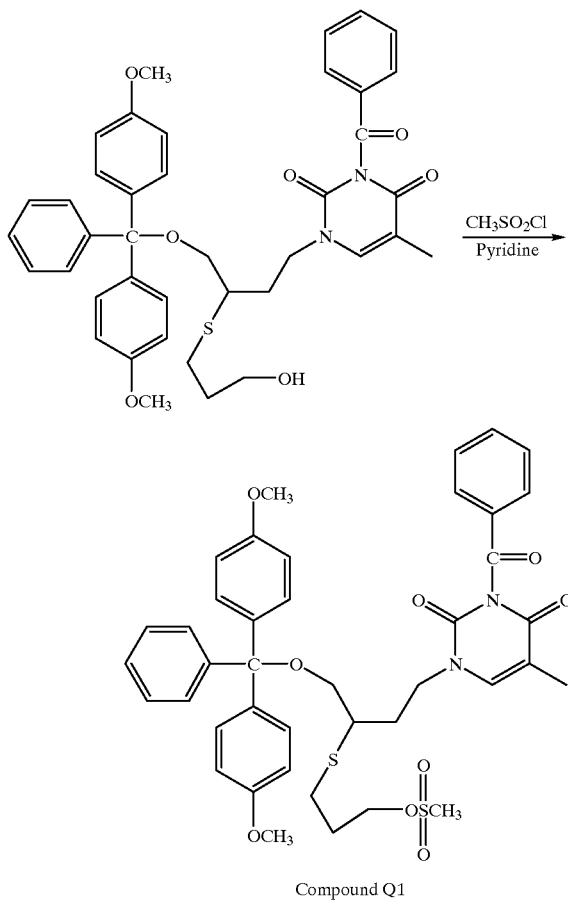

Compound Q1

It will be appreciated that using the above described synthesis, one can produce monomers other than thymine-attached monomer, differing in the nucleobase attached thereto, which monomers, as is exemplified in the following Examples, can be used to synthesize a poly(ether-thioether) nucleic acids compound of a desired preselected sequence.

EXAMPLE 2

Preparation of the Solid Support for Poly(ether-thioether) Nucleic Acid Synthesis Preparation of a CPG-PEG Polymer (Polymer A)

The preferred polymeric support for solid phase poly(ether-thioether) nucleic acids synthesis according to the present invention is a controlled pore glass CPG having particle size of 125–177 microns and which is derivatized by, for example, an alkyl amine chain, e.g., propyl amine, 500 Angstrom (Pierce). To a suspension of the polymer (10 grams) in a mixture of dry DMF and triethylamine (33 ml, 10:1), a solution of succinic anhydride (4 grams) in DMF (20 ml) was added. The reaction mixture was agitated for three hours at room temperature, and the termination of the condensation reaction was monitored by a ninhydrine test. The resulting suspension was filtered and the solid support washed first with methanol (2×100 ml), followed by dry ether (100 ml). To the dry solid support, a solution of 1-dimethoxytrityl-hexaethylene glycol (Compound 1, which is further described under Example 4 below), 4 grams, 6.84 mmoles) in dry dichloromethane (30 ml) and dry pyridine (0.5 ml) were added, followed by addition of 1,3-diisopropylcarbodiimide (1.03 grams, 8.21 mmoles, Aldrich), and dimethylamino pyridine (0.5 grams, 4.09 mmoles). The heterogenic mixture was agitated overnight at room temperature, the resulting PEG-CPG adduct was filtered and washed first with methanol (2×50 ml), second by dichloromethane (2×50 ml) and finally dried by dry ether (2×50 ml). The yield of PEG-CPG adduct was determined following deprotection of the dimethoxytrityl group (DMT) by treating a weighed aliquot of the PEG-CPG adduct with 2 ml of 2% of trichloroacetic acid in dichloromethane for one minute, orange color was monitored spectrophotometrically at 495 nm, resulting in 97% yield.

This process is briefly described by the following reaction schemes:

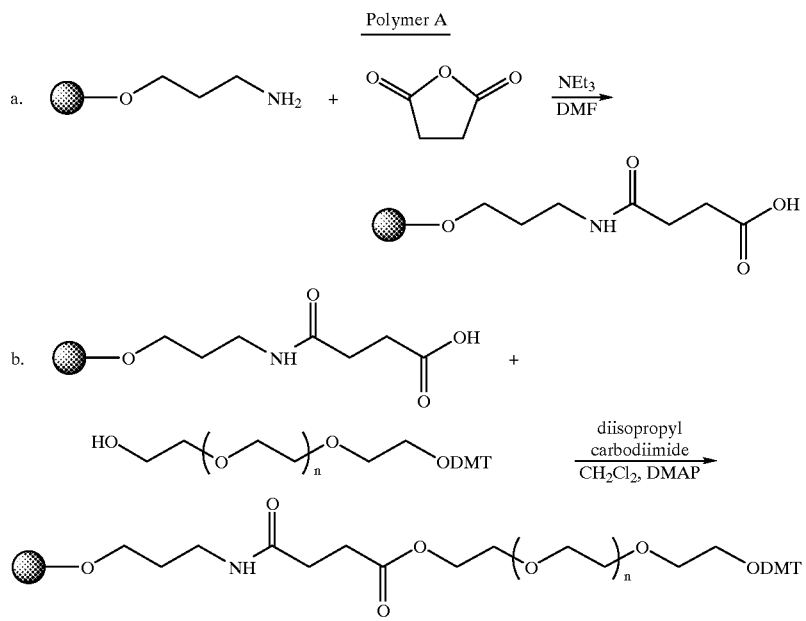

For processes described hereinafter, the following, abbreviations are used:

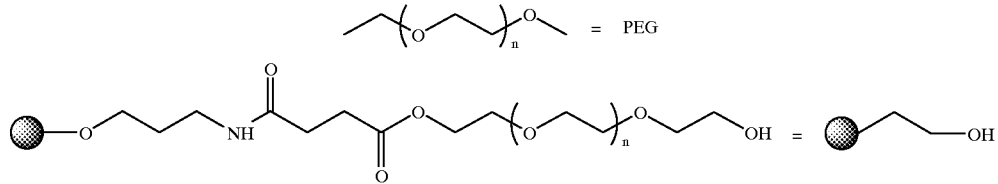

EXAMPLE 3

Poly(ether-thioether) Nucleic Acids Synthesis (The Cycle)

The cycle of poly(ether-thioether) nucleic acids synthesis includes three steps: condensation, capping and deprotection.

Synthesis of Poly(ether-thioether) Nucleic Acids Polythymine

In this example, the poly(ether-thioether) nucleic acids polythyimine could be synthesized using either the Q or the Q1 compounds using otherwise identical conditions, as id further detailed hereinunder.

Condensation

To a suspension of 1 gram of polymer A in 10 ml dry ethylene glycol dimethyl ether (DME) (Aldrich), two ml of 1 M solution of potassium tert-butoxide (Aldrich) in THF, and a solution of 0.5 gram of compound Q or compound Q1 in 2 ml THF were added. The suspension was agitated at room temperature for 1 hour. The resulting polymer-bound Compound Q or Compound Q1 was filtered and was then washed with 25 ml methanol, twice with 25 ml dichloromethane and finally with 25 ml ether.

For processes described hereinafter, the following notation is used:

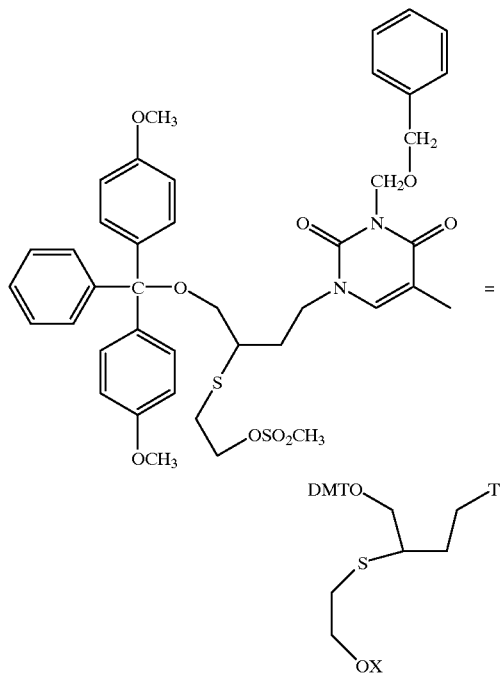

The condensation process (for Compound Q) is briefly described by:

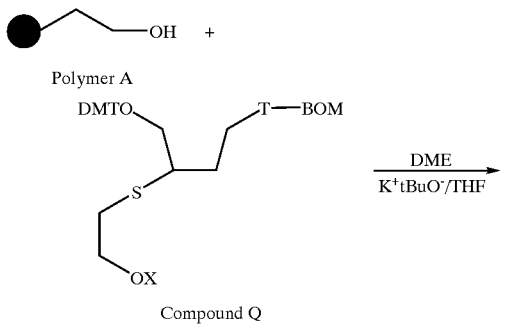

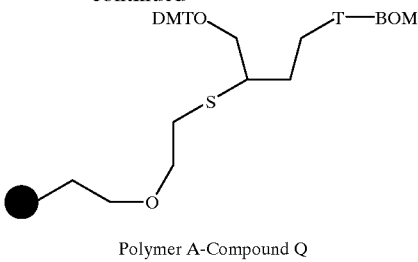

Polymer A-Compound Q

Capping

Acetylation of unreacted polymer hydroxy groups was achieved by adding 10 ml of acetic anhydride/2,6-lutidine/tetrahydrofuran (1/1/8) to the polymeric support resulted from the previous step. The suspension was agitated for five minutes. Then, the solvent was removed by vacuum suction, and the residue was washed twice with 10 ml methanol and twice with 10 ml dichloromethane.

Deprotection of the Dimethoxytrityl Group (DMT)

The dried polymer resulting from any of the two previous steps was treated with 5 ml of 2% of trichloroacetic acid in dichloromethane for one minute, resulting orange color was monitored spectrophotometrically, and the polymer was washed with methanol, dichloromethane and with dried with dry ether.

The deprotection process for poly(ether-thioether) nucleic acid) is briefly described by:

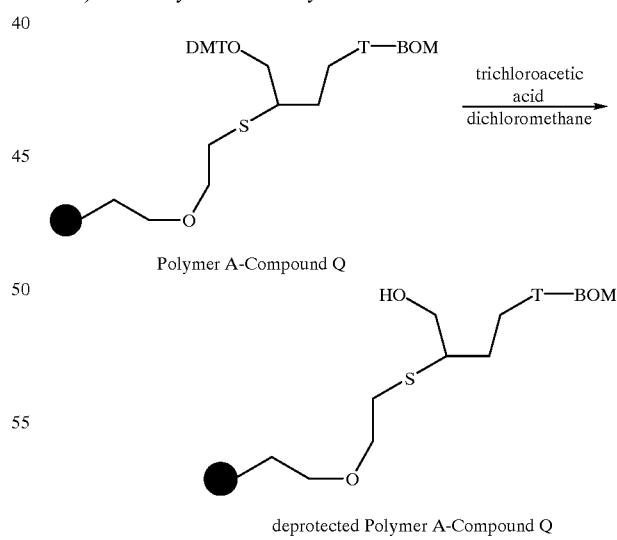

The dried polymer was then condensed with a second Compound Q monomer, in dry DME, in a manner as described above under condensation. The second condensation process, resulting in a thymine-poly(ether-thioether) nucleic acids dimer, is briefly described by:

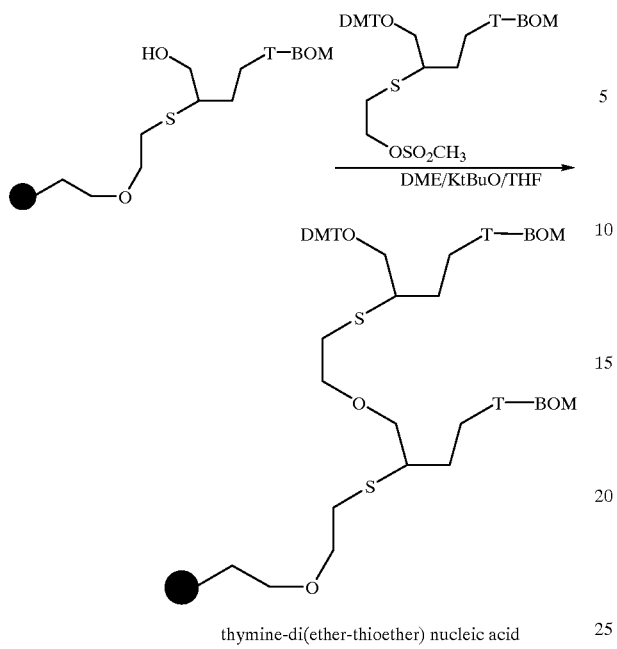

thymine-di(ether-thioether) nucleic acid

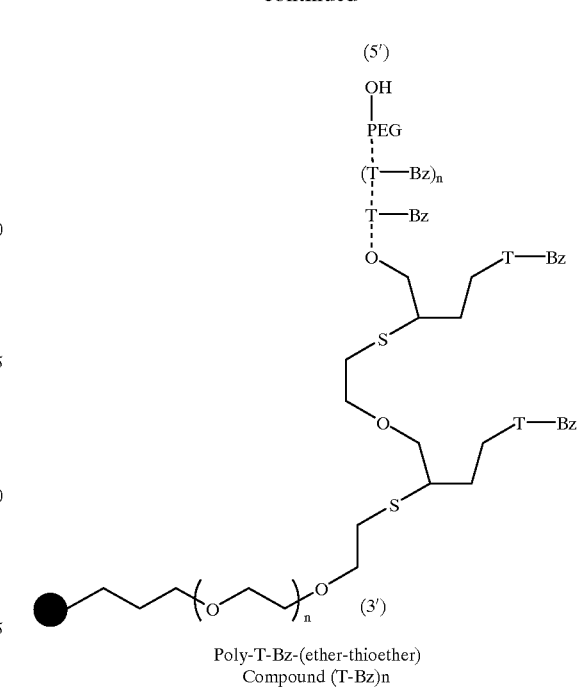

Poly-T-Bz-(ether-thioether)
Compound (T-Bz)n

Such cycles can be repeated as much as needed to form appropriate sense or antisense sequence, wherein in each tri-stages cycle, one additional monomer is sequentially added to the growing chain, up to the desired n cycle.

In this example, the polythymine-poly(ether-thioether)-CPG-PEG adduct is generally describe by:

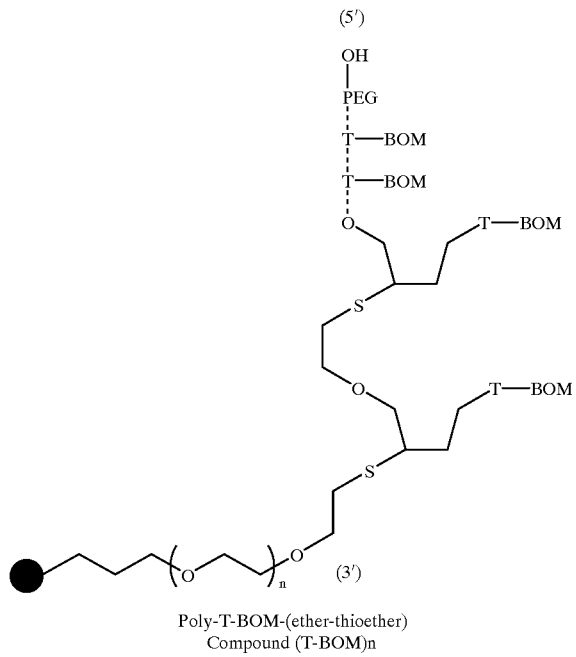

Poly-T-BOM-(ether-thioether)
Compound (T-BOM)n

AND/OR

The 5'—OH remains exposed for the final attachment of the exoconjugate PEG, as described below.

EXAMPLE 4

Preparation of PEG-Exoconjugates

This example applies for both Compounds (T-BOM)n and (T-Bz)n.

Poly(ethylene glycol) (PEG) is a water soluble polymer that when covalently linked to other substrates such as proteins, alters their properties in ways that extent their potential uses. The improved pharmacological performance of PEG-protein conjugates when compared with their unmodified protein counterparts prompted the development of this type of PEG conjugates as therapeutic agents. For example, enzyme deficiencies, e.g., adenine deaminase (ADA) deficiency, for which therapy with native enzymes was found inefficient due to rapid clearance and/or immunological reactions can now be treated with equivalent PEG-enzymes, e.g., PEG-ADA. This novel observation may open new horizons to the application of PEGylation technology.

Condensation of a Second PEG Exoconjugate in the Last n Cycle

Preparation of 4,4'-dimethoxytrityl-hexaethylene Glycol (Compound 1)

To a solution of hexaethylene glycol (8.46 grams, 30 mmoles) in 250 ml dry pyridine, a solution of 4,4-dimethoxytrityl chloride (3.38 grams, 10 mmoles) in 50 ml dry pyridine was added dropwise at room temperature. The resulting solution was stirred at room temperature for additional 5 hours. The solvent was then evaporated to dryness, and the residue was extracted with 200 ml ethylacetate/200 ml 5% sodium bicarbonate solution, washed twice with water and twice with brine solution. The obtained organic layer was dried over anhydrous sodium sulfate, evaporated and purified by silica gel column chromatography using 5% methanol in dichloromethane, 0.5% pyridine. The resulting 4,4-dimethoxytrityl-hexaethylene glycol compound (5.23 grams, 89% yield) migrated with Rf=0.29.

This process is briefly described by:

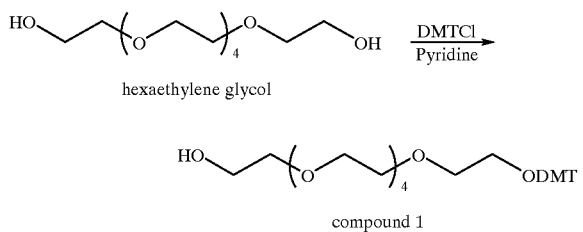

was extracted with 200 ml of ethylacetate/200 ml of 5% sodium bicarbonate solution, washed twice with water and twice with brine solution. The obtained organic layer was dried over anhydrous sodium sulfate, evaporated and purified by silica gel column chromatography using ethylacetate/hexane (4/1), 0.5% pyridine. The resulting Compound 2 (6.12 grams, 92% yield) migrated with Rf=0.31.

This process is briefly described by:

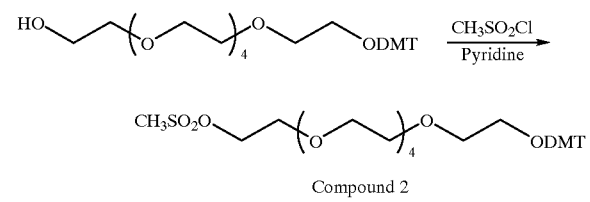

Preparation of 1-methane sulfonate,6-(4,4-dimethoxytrityl)-hexaethylene glycol (Compound 2)

To a solution of Compound 1 (5.84 grams, 10 mmoles) in 100 ml dry pyridine, under argon, methanesulfnyl chloride (1.36 grams, 0.94 ml, 12 mmoles) was added by injection. The is reaction was stirred overnight at room temperature. The solvent was then evaporated to dryness, and the residue Compound 2 was condensed to the last base in the growing chain after detritylation as described under Example 3 above.

The final product of the poly(ether-thioether) nucleic acid polythymine synthesis after the addition of second PEG moiety is represented by:

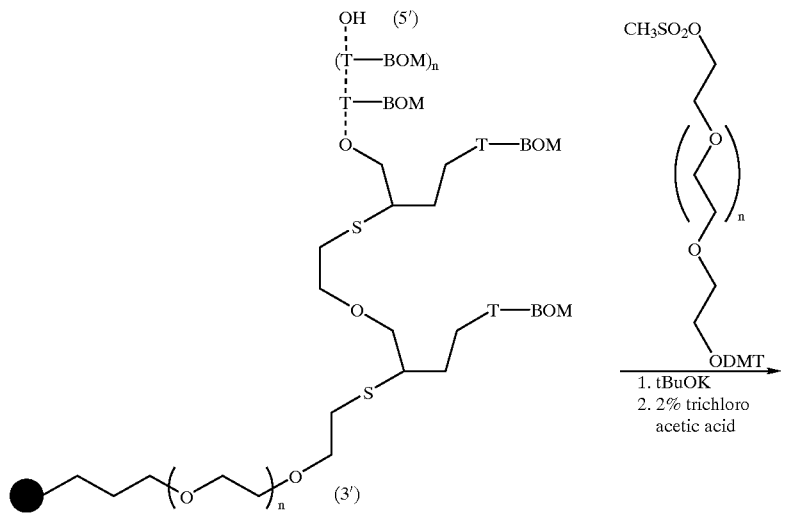

-continued

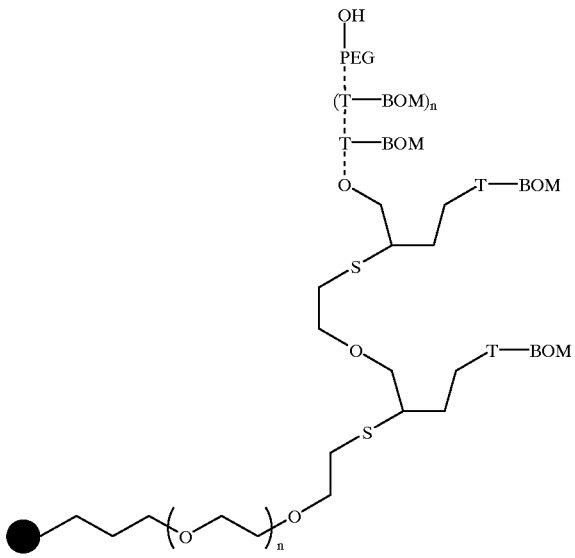

EXAMPLE 5

Generation of Poly(ether-sulfone) Nucleic Acid (optional)

In addition to poly(ether-thioether) nucleic acids, another polymer poly(ether-sulfone) nucleic, can be prepared by adding an additional step, by oxidizing the sulfide moiety to sulfone. To 1 gram of a polymeric support to which the poly(ether-thioether) is still attached, a solution of N-methylmorpholine-N-oxide (309 mg, 2.28 mmol, Aldrich) in 5 ml acetone and 1 ml water was added. To this heterogenic solution, 42 microliters of 0.18 molar aqueous $OSO_4$ (0.0076 mmol, 1 mol, Aldrich) was added. The mixture was agitated at room temperature for 12 hours and was subsequently quenched by addition of 5 ml of saturated aqueous sodium bisulfite.

The polymeric support was filtered and washed with water (20 ml), methanol (30 ml), dichloromethane (20 ml) and finally with ether (20 ml). The dried residue is now ready for the step of deprotection of the dimethoxy trityl group for the preparation of 5'-PEG-exoconjugates.

This reaction is briefly described by:

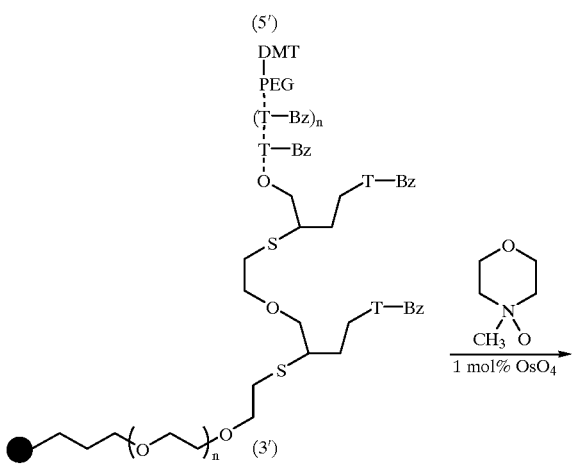

-continued

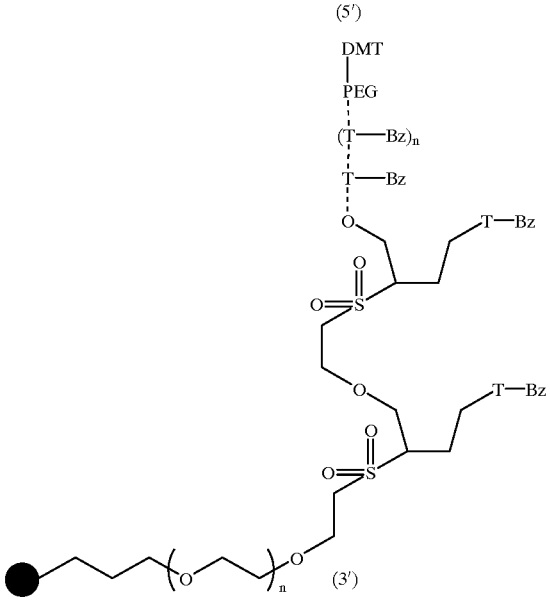

The rational for this modification is to conserve some rigidity in the backbone by chelating metal cations with three oxygen atoms, and also to enhance cellular uptake by increasing the positive charge of the molecule.

Generation of Poly(ether-sulfoxide) Nucleic Acid (optional)

In addition to poly(ether-thioether) nucleic acid, and to poly(ether-sulfone) nucleic acid derived therefrom by oxidation, another oxidized polymer, i.e., poly(ether-sulfoxide) nucleic acid, can be prepared by employing a step of oxidizing the sulfide molety of poly(ether-thioether) nucleic acid to sulfoxide.

To 1 gram of a polymeric support to which the poly(ether-thioether) is still attached, a solution of metachloroperbenzoic acid (172 milligrams, 1 mmol, Aldrich) in 5 ml of dichloromethane was added. The mixture was agitated at room temperature for 12 hours and was subsequently quenched by addition of 5 ml of saturated aqueous sodium bisulfite.

The polymeric support was filtered and washed with water (20 ml), methanol (30 ml), dichloromethane (20 ml) and finally with ether (20 ml). The dried residue is now ready for the step of deprotection of the dimethoxy trityl group for the preparation of 5'-PEG-exoconjugates.

This reaction is briefly described by:

EXAMPLE 6

Deprotection and Detachment

When cycling (condensation) is completed, few general deprotection steps are performed as follows:

Deprotection of Amino Groups Containing Bases

Deprotection of Compound (T-BOM)n-PEG is achieved by hydrogenation. To the poly(ether-thioether) nucleic acid attached to the polymeric support, 10 ml of tetrahydrofuran, 100 milligrams of 5% Pd/C were added and $H_2$ (1 atmospheric pressure) was applied for 2 hours at room tempera-

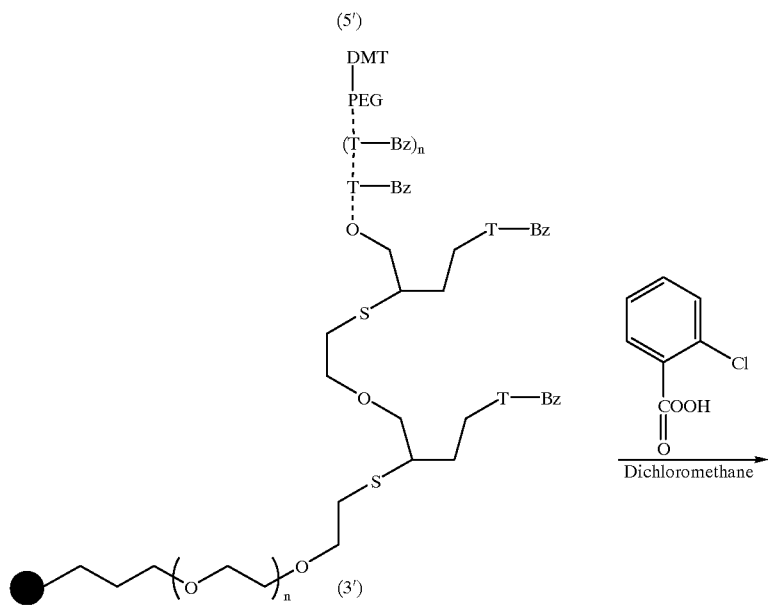

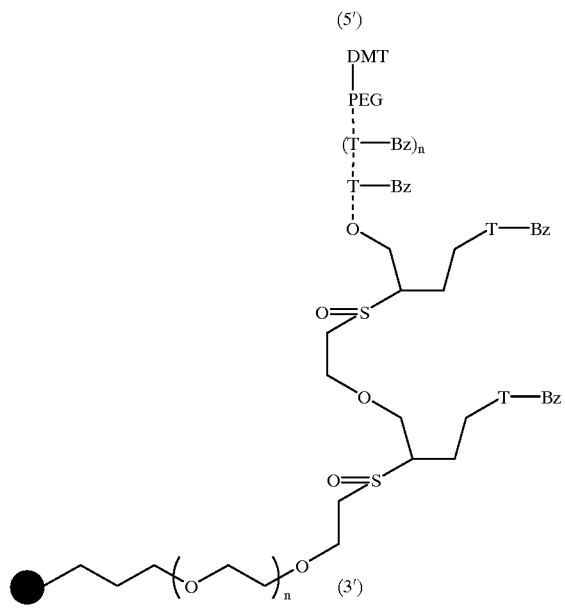

ture. The polymeric support was then filtered, washed with methanol (2×30 ml) and dry ether (2×30 ml).

This process is briefly described by:

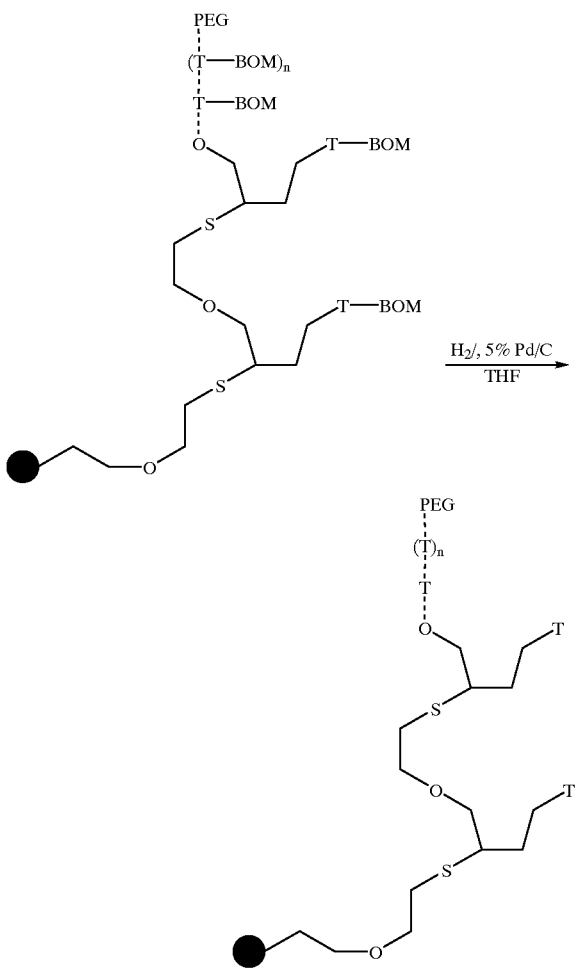

Detachment of the Poly(ether-thioether) From the Solid Support

In this example the benzoate protecting group is also removed. The dry polymeric support, obtained in the previous step, was subjected to concentrated ammonium hydroxide for 16 hours at 55° C., centrifuged and the supernatant was collected.

EXAMPLE 7

Synthesis of Chirally-pure Monomers for Synthlesizing Poly(ether-thioether) Nucleic Acids According to the Present Invention Preparation of a Stereo-specific Monomer Described by Formula E Preparation of the S stereo-specific isomer of poly(ether-thioether) nucleic acids is based on an asymmetric starting material, (S)-(−) Dimethyl malate, for the preparation of the herein described Compound E. Additional consecutive synthesis steps are as follows:

Preparation of (S)-1,2,4-butanetriol (Compound I)

A solution of (S)-(−)-dimethyl malate (Aldrich) (25.9 g, 159 mmoles) in 100 ml dry tetrahydrofuran was dropwise added to a solution of lithium aluminum hydride (21 grams, 553 mmoles) in 1 liter of dry tetrahydrofuran under argon. The reaction mixture was refluxed overnight, followed by an addition of water (160 ml) and 10% sulfuric acid (100 ml). The white precipitate formed was filtered and washed with dry ethanol (4×130 ml). The combined portions were evaporated to near dryness under vacuo. The inorganic material contained in the residual oil was removed by short column chromatography over 50 grams silica gel, with chloroform-ethanol mixture 560 ml (3:1 v/v) and 670 ml (2:1 v/v) as an eluent. The solvent was removed, and Compound I as a light yellow oil was obtained (12 grams, 60 % yield). NMR-(pyridine): 2.14 (m, 2H), 3.97 (dd, J=5 Hz, 2H), 4.17 (dt, J=5, J=6 Hz, 2H), 5.38 (m, 1H), 6.00 (hydroxyls, 3H).

This process is briefly described by:

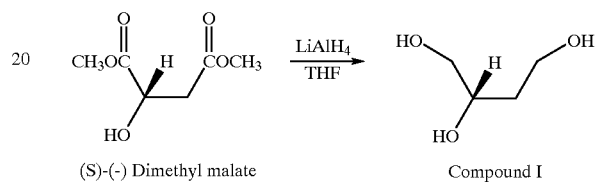

Preparation of (S)-1,2-O-Isopropylidenebutane-1,2,4-triol (Compound II)

(S)-1,2,4-butanetriol (9 grams, 85.7 mmoles) was stirred in acetone (500 ml) and p-toluenesulfonic acid (400 mgrams) at room temperature for 1.5 hours. Sodium bicarbonate (2 grams) was then added to the reaction mixture, and stirring was continued for additional 10 minutes. The solvent was evaporated to dryness, and the residue was extracted with 200 ml ethylacetate/200 ml water, washed twice with water and twice with brine solution. The obtained organic layer was dried over anhydrous sodium sulfate, evaporated and purified by silica gel column chromatography using hexane/ethylacetate (2/1). The resulting Compound III, as a colorless oil (11.6 grams, 95% yield) migrated with Rf=0.47. NMR (CDCl$_3$): 1.36 (s, 3H), 1.39 ( s, 3H), 1.81 (dt, J=5.5, J=6 Hz, 2H), 3.10 (br s , 1H), 3.58 (dd, J=7, J=7.5 Hz, 1H), 3.75 ( t, J=6 Hz, 2H), 4.07 (dd, J=6, J=7 Hz, 1 H), 4.26 (m, 1H).

This process is briefly described by:

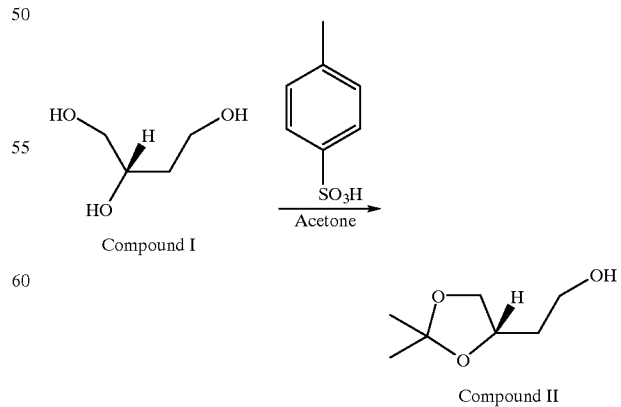

Preparation of (S)-4-O-acetate-1,2-O-isopropylidene-1,2,4-butanetriol (Compound III)

A solution of the Compound II (14.6 grams, 100 mmoles), in dry pyridine (100 ml) and acetic anhydride (100 ml) was stirred for 3 hours at room temperature. The solvent was evaporated to dryness, and the residue was extracted with 200 ml of ethylacetate/200 ml water, washed twice with water and twice with brine solution. The obtained organic layer was dried over anhydrous sodium sulfate, evaporated and purified by silica gel column chromatography using hexane/ethylacetate (1/2). The resulting Compound III, as a colorless oil (18.0 grams, 95% yield) migrated with Rf=0.35. NMR (CDCl$_3$): 1.35 (s, 3H), 1.41 (s, 3H), 2.02 (m, 2H), 3.59 (dd, J=7, J=7.5 Hz, 1H), 3.75 (t, J=6 Hz, 2H), 4.21 (m, 2H).

This process is briefly described by:

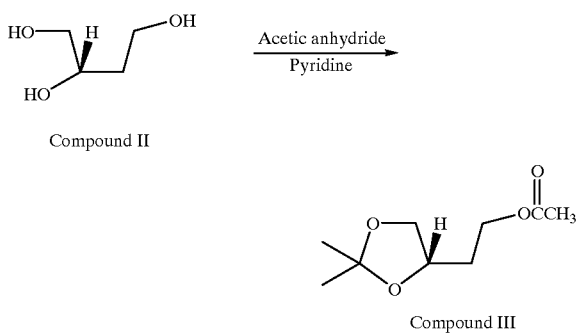

Preparation of (S)-4-O-acetyl-1,2,4-butanetriol (Compound IV)

Compound III (18.83 grams, 100 mmoles) was dissolved in 80% aqueous acetic acid (200 ml) and kept at room temperature for 21 hours, followed by additional 4 hours at 50° C. Evaporation, followed by co-evaporation with toluene (2×50 ml) afforded the isolation of Compound IV (11.2 grams, 75% yield). NMR (CDCl$_3$): 1.76 (m, 2H), 2.06 (s, 3H), 3.45 (m, 1H), 3.62 (m, 1H), 3.79 (m, 1H), 4.21 (m, 2H), 4.75 (s, broad, 1H).

This process is briefly described by:

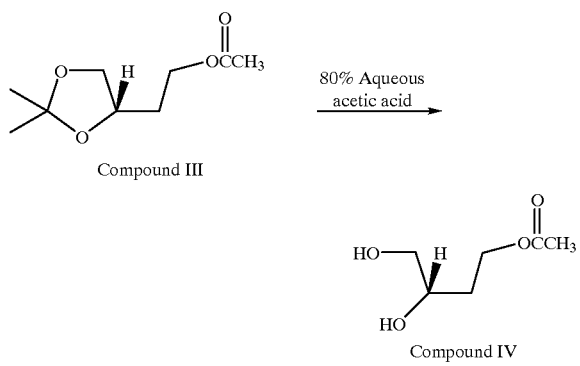

Preparation of (S)-1-O-(4,4'-dimethoxytrityl)-4-O-acetyl-1,2,4-butanetriol (Compound V)

Compound IV (14.81 grams, 100 mmoles) was co-evaporated with dry pyridine (2×50 ml), and the residue oil was redissolved in 200 ml dry pyridine. The resulting solution was cooled to 0° C., and dimethoxytrityl chloride (37.23 grams, 120 mmoles) in dry pyridine (100 ml) was dropwise added, while stirring, under argon. The solution was then allowed to warm to room temperature, and stirred for additional 18 hours. The solvent was evaporated to dryness, and the residue was extracted with 200 ml ethylacetate/200 ml water, washed twice with water and twice with brine solution. The obtained organic layer was dried over anhydrous sodium sulfate, evaporated and purified by silica gel column chromatography using hexane/ethylacetate (2/1). The resulting Compound V (38.2 grams, 84.8% yield) migrated with Rf=0.29. NMR (CDCl$_3$): 1.71 (m, 2H), 2.01 (s, 3H), 3.15 (m, 2H), 3.78 (s, 6H), 4.13 (m, 2H), 6.79–7.45 (m, 13H).

This process is briefly described by:

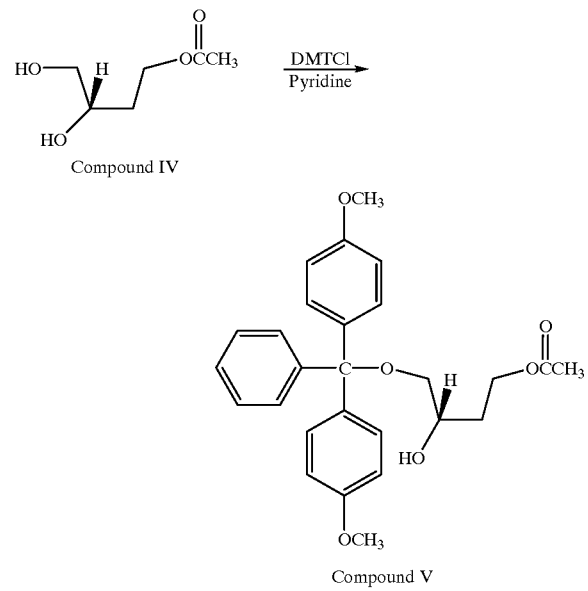

Preparation 2-bromo-tertbutyl-dimetlhylsilyl ethanol (Compound VI)

To a solution of 2-bromoethanol (17.27 grams, 138 mmoles), and imidazole (23.48 grams, 345 mmoles) in dry dichloromethane (200 ml), a solution of tert-butyldimethylsilyl chloride (25 grams, 165 mmoles) in dry dichloromethane (100 ml) was dropwise added. After stirring for two hours at room temperature, the solvent was evaporated to dryness, and the residue was extracted with 400 ml of ethylacetate/200 ml 5% NaHCO$_3$ solution, washed twice with water and twice with brine solution. The obtained organic layer was dried over anhydrous sodium sulfate, evaporated and purified by silica gel column chromatography using hexane/ethylacetate (10/1). The resulting Compound VI (29.15 grams, 88.6% yield) migrated with Rf=0.53. NMR (CDCl$_3$): 0.07 (s, 6H), 0.86 (s, 9H), 3,38 (t, 2H), 3.88 (t, 3H).

This process is briefly described by:

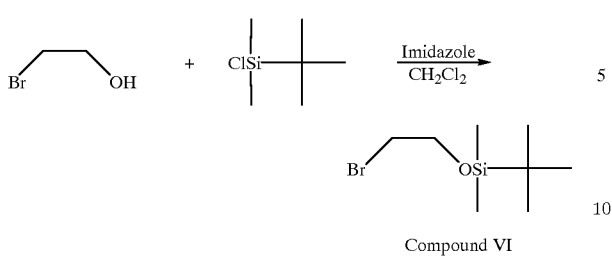

Compound VI

Preparation of 2-S-acetyl-tertbutyl-dimethylsilyl ethanol (Compound VII)

To a solution of Compound VI (23.9 grams, 10 mmoles) in 150 ml dry DMF, potassium thioacetate (14.82 grams, 13 mmoles) was added. The reaction mixture was heated to 110° C. for 4 hours. The solvent was evaporated to dryness, and the residue was extracted with 400 ml of ethylacetate/200 ml of water and twice with brine solution. The obtained organic layer was dried over anhydrous sodium sulfate, evaporated and purified by silica gel column chromatography using hexane/ethylacetate (10/1). The resulting Compound VII (22.81 grams, 97.4% yield) migrated with Rf=0.38. NMR (CDCl$_3$): 0.032 (s, 6H), 0.85 (s, 9H), 2.29 (s, 3H), 2.99 (t, 2H), 3.68 (t, 2H).

This process is briefly described by:

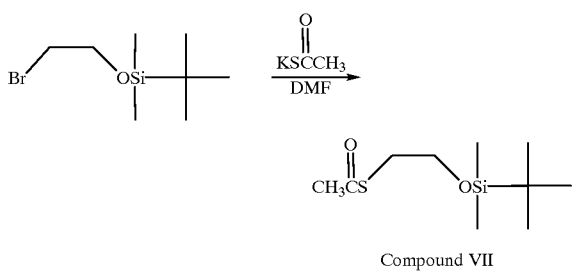

Compound VII

Preparation of 2-mercapto-tertbutyl-dimethylsilyl ethanol (Compound VIII)

Compound VII (23.4 grams, 100 mmoles), were mixed with 100 ml solution of 2N NaOH in methanol. After stirring at room temperature for 2 hours under argon, the basic solution was neutralized with 6N HCl, to pH 7.0. The solvent was evaporated to dryness, and the residue was extracted with 400 ml of ethylacetate/200 ml of water and twice with brine solution. The obtained organic layer was dried over anhydrous sodium sulfate, evaporated and was used for the next step without further purification. The resulting Compound VIII (18.5 grams, 96.2% yield), was analyzed by TLC-(hexane/ethyl acetate-(2/1) and migrated with Rf=0.22.

This process is briefly described by:

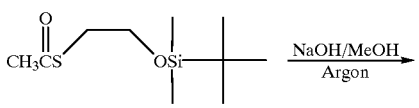

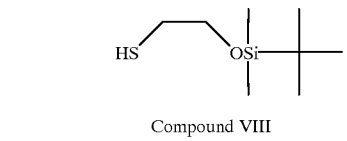

Compound VIII

Preparation of (R)-Compound E

Diethyl azodicarboxylate (Aldrich, 6.96 grams, 40 mmoles), was added to a well stirred solution of triphenylphosphine (10.50 grams, 40 mmoles) in dry tetrahydrofuran (100 ml) at 0° for 30 minutes, resulting in a slurry yellowish solution. Compound V (9.0 grams, 20 mmoles) in THF (50 ml) was then added and the reaction was stirred for additional 10 minutes at 0°. Compound VIII (7.68 grams, 40 mmoles) in THF was dropwise added to the reaction over a time period of 10 minutes and the mixture was stirred for 1 hour at 0°, followed by 1 hat room temperature. The resulting clear yellow solution was concentrated and was then subjected to hydrolysis with aqueous concentrated ammonia (100 ml) and THF (50 ml) for 2 hours at room temperature. The solvent was evaporated to dryness, and the residue was extracted with 400 ml of ethylacetate/200 ml of water and twice with brine solution. The obtained organic layer was dried over anhydrous sodium sulfate, evaporated and purified by silica gel column chromatography using hexane/ethylacetate (10/1). The resulting (R)-Compound D was then purified by column chromatography over silica gel using conditions as described hereinabove for the preparation of (R/S)-Compound D. The resulting (R)-Compound E (9.30 grams, 79.8%) has an Rf value and NMR spectra which are identical to the above described (R/S)-Compound E (see Example 1).

This process is briefly described by:

a.

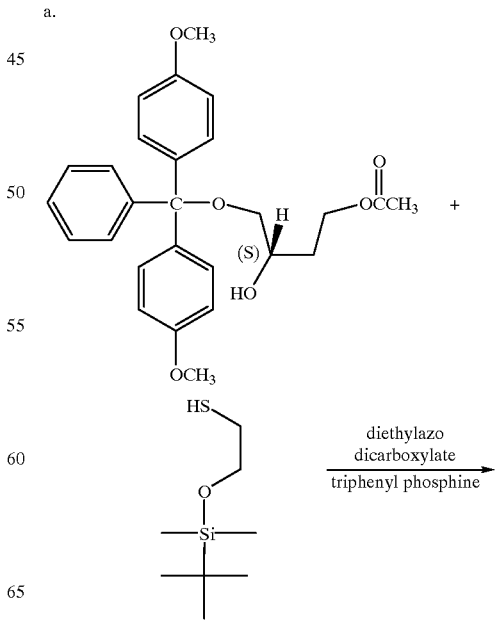

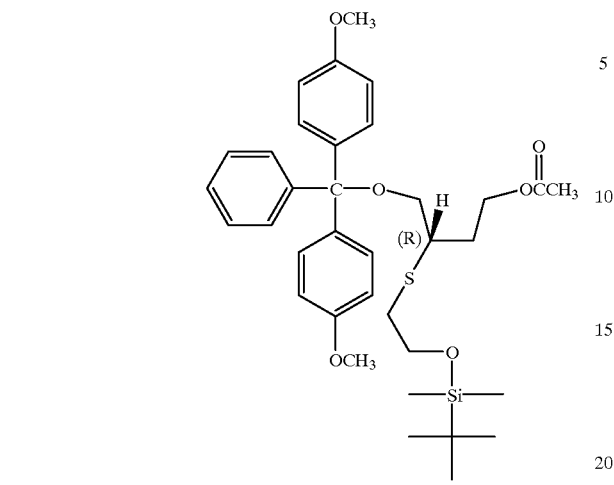

b.

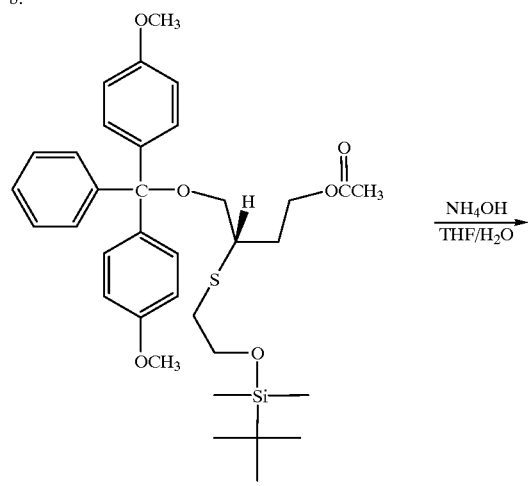

(R)-ompound D

NH₄OH / THF/H₂O →

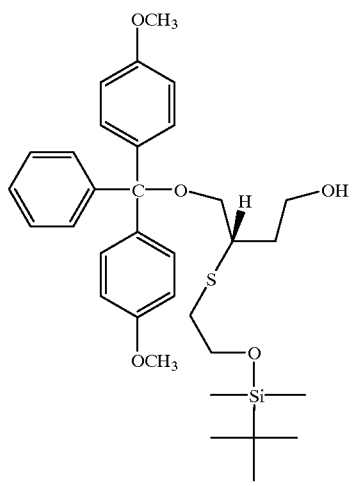

(R)-Compound E

Synthesis steps of an (R)-Compound Q from the (R)-Compound E are as hereinabove described in Example 1 for the synthesis of Compound Q to Compound E.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

What is claimed is:

1. A compound having the formula:

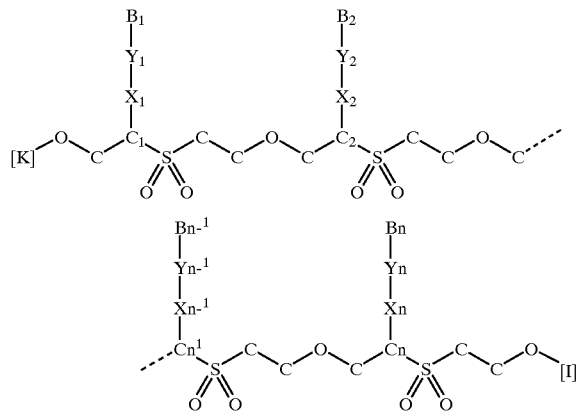

wherein:
n is an integer greater than one;
each of $B_1$, $B_2$, $B_{n-1}$ and $B_n$ is a chemical functionality group independently selected from the group consisting of a naturally occurring nucleobase and a nucleobase binding group;
each of $Y_1$, $Y_2$, $Y_{n-1}$ and $Y_n$ is a first linker group;
each of $X_1$, $X_2$, $X_{n-1}$ and $X_n$ is a second linker group;
$C_1$, $C_2$, $C_{n-1}$ and $C_n$ are chiral carbon atoms; and
[K] and [I] are a first and a second exoconjugates.

2. The compound of claim 1, wherein each of said $Y_1$-$X_1$, $Y_2$-$X_2$, $Y_{n-1}$-$X_{n-1}$ and $Y_n$-$X_n$ first-second linker groups is a single bond.

3. The compound of claim 1, wherein each of said $Y_1$, $Y_2$, $Y_{n-1}$ and $Y_n$ first linker groups is independently selected from the group consisting of an alkyl group, a phosphate group, a (C2–C4) alkylene chain, a (C2–C4) substituted alkylene chain and a single bond.

4. The compound of claim 1, wherein each of said $Y_1$, $Y_2$, $Y_{n-1}$ and $Y_n$ first linker groups is independently selected from the group consisting of a methylene group and a C-alkanoyl group.

5. The compound of claim 1, wherein each of said $X_1$, $X_2$, $X_{n-1}$ and $X_n$ second linker groups is independently selected fr consisting of a methylene group, an alkyl group, an amino group, an amido group, a sulfur atom, an oxygen atom, a selenium atom, a C-alkanoyl group, a phosphate derivative group, a carbonyl group and a single bond.

6. The compound of claim 1, wherein m percents of said chiral carbons are in an S configuration, wherein m is selected from the group consisting of 90–95%, 96–98%, 99% and greater than 99%.

7. The compound of claim 1, wherein [K] and [I] are each a polyethylene glycol moiety.

8. A compound as in claim 1, having the formula:

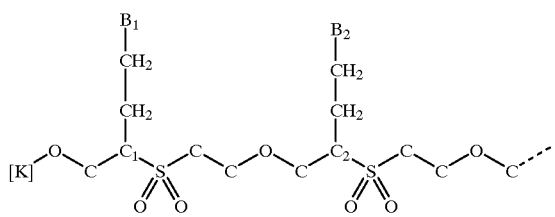

-continued

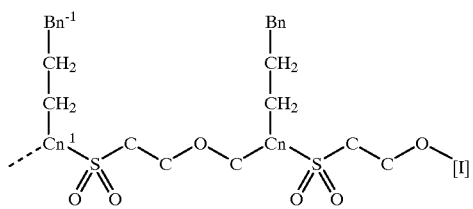

9. A process of preparing a compound which comprises a poly(ether-sulfone) backbone having a plurality of chiral carbon atoms, said poly(ether-sulfone) backbone bearing a plurality of ligands being individually bound to said chiral carbon atoms, said ligands including a moiety selected from the group consisting of a naturally occurring nucleobase and a nucleobase binding group, the process comprising:

(a) obtaining monomers each of said monomers having an ether moiety and a thioether moiety, said ether moiety including at least one etheric bond, said thioether moiety including at least one thioetheric bond, each of said monomers further including at least one chiral carbon atom to which a functionality group being linked, said functionality group being selected from the group consisting of a naturally occurring nucleobase and a nucleobase binding group;

(b) attaching a first monomer of said monomers to a solid support;

(c) sequentially condensing monomers in a predetermined sequence to said first monomer for obtaining a polymer of condensed monomers; and (d) oxidizing sulfide moieties to sulfone.

10. The process of claim 9, wherein said chiral carbon atoms are separated from one another in said backbone by from four to six intervening atoms.

11. A pharmaceutical composition comprising, as an active ingredient, a compound according to claim 1, and at least one pharmaceutically effective carrier, binder, thickener, diluent, buffer, preservative or surface active agent.

* * * * *

UNITED STATES PATENT AND TRADEMARK OFFICE
CERTIFICATE OF CORRECTION

PATENT NO. : 6,348,583 B1
DATED : February 19, 2002
INVENTOR(S) : Segev

It is certified that error appears in the above-identified patent and that said Letters Patent is hereby corrected as shown below:

<u>Column 68,</u>
Line 43, delete "fr" and in its place insert -- from the group --.

Signed and Sealed this

Third Day of September, 2002

Attest:

Attesting Officer

JAMES E. ROGAN
*Director of the United States Patent and Trademark Office*